(12) United States Patent
Ostareck-Lederer et al.

(10) Patent No.: US 9,745,369 B2
(45) Date of Patent: Aug. 29, 2017

(54) MODULATION OF TLR4-SIGNALING PATHWAY

(71) Applicant: Rheinisch-Westfalische Technische, Aachen (DE)

(72) Inventors: Antje Ostareck-Lederer, Aachen (DE); Dirk Ostareck, Aachen (DE); Gernot Marx, Aachen (DE); Anke Liepelt, Aachen (DE); Jana Kloos, Dusseldorf (DE)

(73) Assignee: Rheinisch-Westfalische Technische, Aachen (DK)

( * ) Notice: Subject to any disclaimer, the term of this patent is extended or adjusted under 35 U.S.C. 154(b) by 59 days.

(21) Appl. No.: 14/405,717

(22) PCT Filed: May 22, 2013

(86) PCT No.: PCT/EP2013/001513
§ 371 (c)(1),
(2) Date: Dec. 4, 2014

(87) PCT Pub. No.: WO2013/182273
PCT Pub. Date: Dec. 12, 2013

(65) Prior Publication Data
US 2015/0152171 A1 Jun. 4, 2015

(30) Foreign Application Priority Data
Jun. 4, 2012 (EP) .................................... 12004251

(51) Int. Cl.
| | |
|---|---|
| *C12N 15/113* | (2010.01) |
| *C07K 16/18* | (2006.01) |
| *C07K 14/705* | (2006.01) |
| *C07K 14/47* | (2006.01) |
| *A61K 38/02* | (2006.01) |
| *A61K 38/43* | (2006.01) |
| *C07K 2/00* | (2006.01) |
| *C12N 9/00* | (2006.01) |
| *C12N 15/115* | (2010.01) |

(52) U.S. Cl.
CPC .............. *C07K 16/18* (2013.01); *A61K 38/02* (2013.01); *A61K 38/43* (2013.01); *C07K 2/00* (2013.01); *C07K 14/47* (2013.01); *C07K 14/70596* (2013.01); *C12N 9/00* (2013.01); *C12N 15/113* (2013.01); *C12N 15/115* (2013.01); *C07K 2317/76* (2013.01); *C12N 2310/14* (2013.01); *C12N 2310/16* (2013.01); *C12N 2320/30* (2013.01)

(58) Field of Classification Search
None
See application file for complete search history.

(56) References Cited

U.S. PATENT DOCUMENTS

2010/0317840 A1* 12/2010 Chen .................... C12N 15/113
536/24.5

OTHER PUBLICATIONS

Tchorzewski et al., Expression of Toll-Like Receptors on Human Rectal Adenocarcinoma Cells. Arch. Immunol. Ther. Exp. (2014) 62:247-251.*
Thisted et al., Optimized RNA Targets of Two Closely Related Triple KH Domain Proteins, Heterogeneous Nuclear Ribonucleoprotein K and aCP-2KL, Suggest Distinct Modes of RNA Recognition. JBC, vol. 276, No. 20, Issue of May 18, pp. 17484-17496, 2001.*
Yoo et al., Interaction of N-WASP with hnRNPK and Its Role in Filopodia Formation and Cell Spreading. The Journal of Biological Chemistry vol. 281, No. 22, pp. 15352-15360, Jun. 2, 2006.*
Takahisa Hirose et al.; "The Orphan Receptor TAK1 Acts as a Repressor of RAR-, RXR- and T3R-Mediated Signaling Pathways"; Biochemical and Biophysical Research Communications; Jun. 6, 1995; pp. 83-91; vol. 211, No. 1.
PCT International Search Report for PCT/EP2013/001513 issued on Sep. 9, 2013.
Roberto Benelli et al.; "Novel Antivascular Efficacy of Metronomic Docetaxel Therapy in Prostate Cancer: hnRNP K as a Player"; International Journal of Cancer; Jun. 15, 2009; pp. 2989-2996; vol. 124, No. 12.
Y Liu et al.; "Heterogeneous Nuclear Ribonucleoprotein K, an RNA-Binding Protein, is Required for Optic Axon Regeneration in Xenopus Laevis"; Journal of Neuroscience; Mar. 7, 2012; pp. 3563-3574; vol. 32, No. 10.
I. S. Naarmann et al.; "mRNA Silencing in Human Erythroid Cell Maturation: Heterogeneous Nuclear Ribonucleoprotein K Controls the Expression of its Regulator c-Src"; Journal of Biological Chemistry; Jun. 1, 2008; pp. 18461-18472; vol. 283, No. 26.
X. Wittebole et al; "Toll-Like Receptor 4 Modulation as a Strategy to Treat Sepsis"; Mediators of Inflammation; Jan. 1, 2010; pp. 1-9; vol. 2010.
Mona Hedayat et al; "Prophylactic and Therapeutic Implications of Toll-Like Receptor Ligands"; Medicinal Research Reviews; Mar. 1, 2012; pp. 294-325; vol. 32, No. 2.
Guha et al., "LPS induction of gene expression of human monocytes" Cellular Signalling 13 (2001) 85-94 (10 pages).
Hotchkiss et a., "The Pathophysiology and Treatment of Sepsis" New England Journal of Medicine, Jan. 9, 2003, 138-150 (13 pages).
Zanotti et al., "Cytokine modulation in sepsis and septic shock" Expert Opinion on Investigational Drugs (2002) 11:8, 1061-1075 (16 pages).

* cited by examiner

*Primary Examiner* — Kevin Hill
*Assistant Examiner* — Arthur S Leonard
(74) *Attorney, Agent, or Firm* — Colin P. Cahoon; Shaukat A. Karjeker; Carstens & Cahoon, LLP

(57) ABSTRACT

The present invention relates to compounds for use in modulating the toll-like receptor 4 (TLR4) signaling pathway, as well as to a pharmaceutical composition comprising said compounds.

4 Claims, 32 Drawing Sheets

A)

B)

Figure 14:
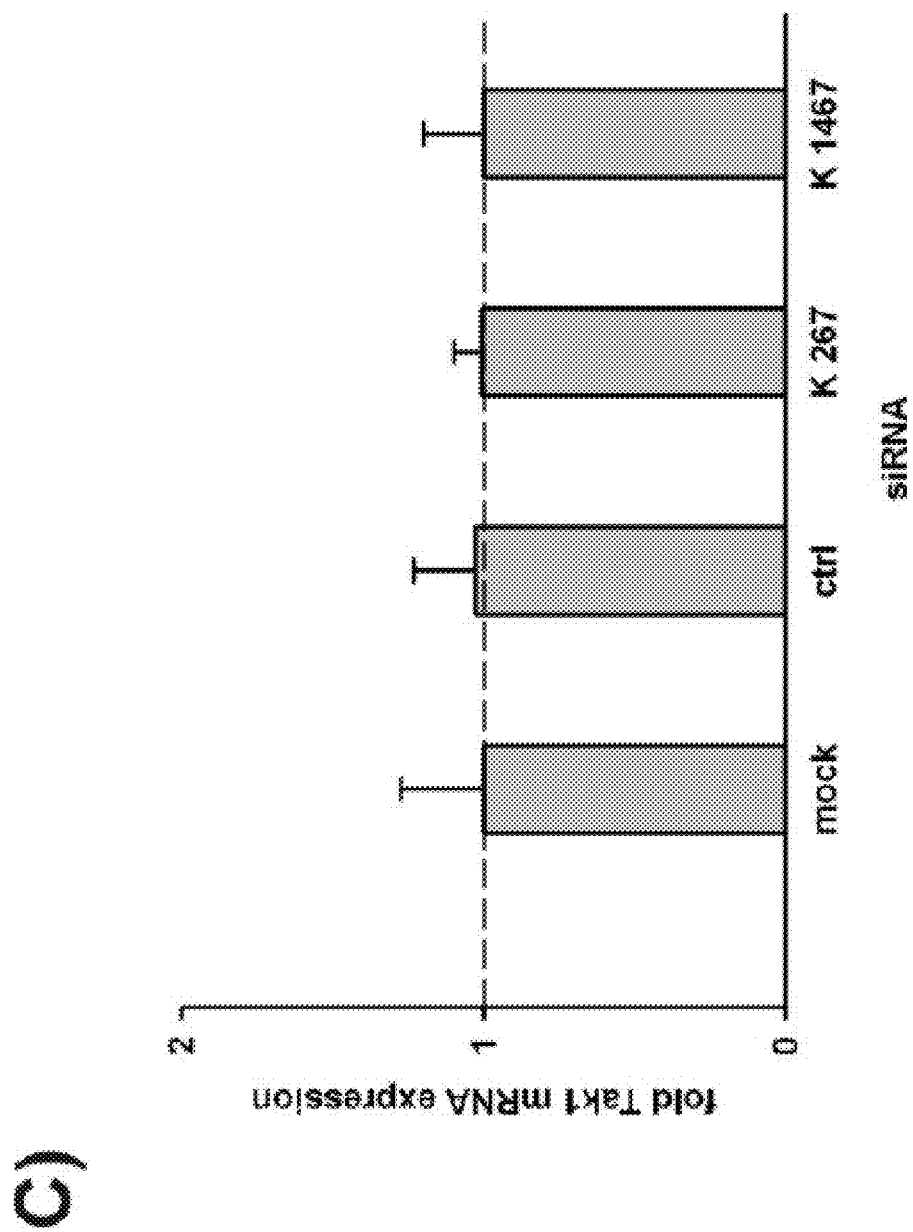

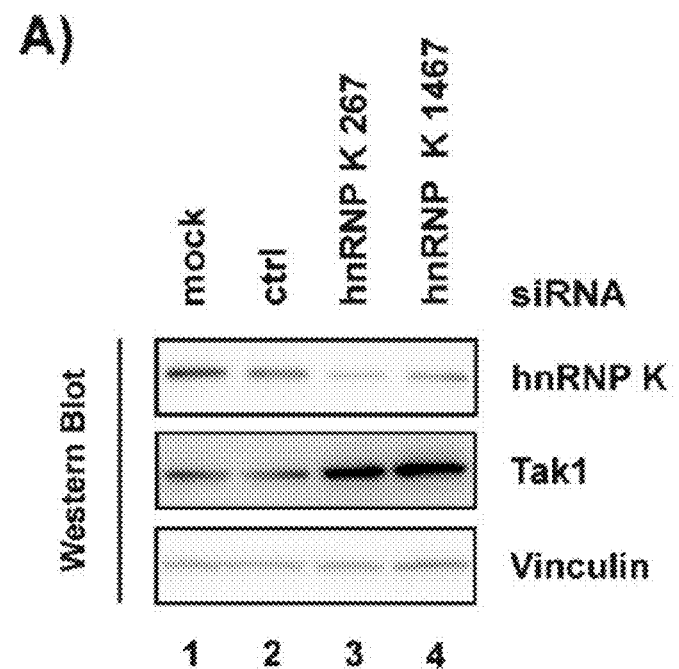
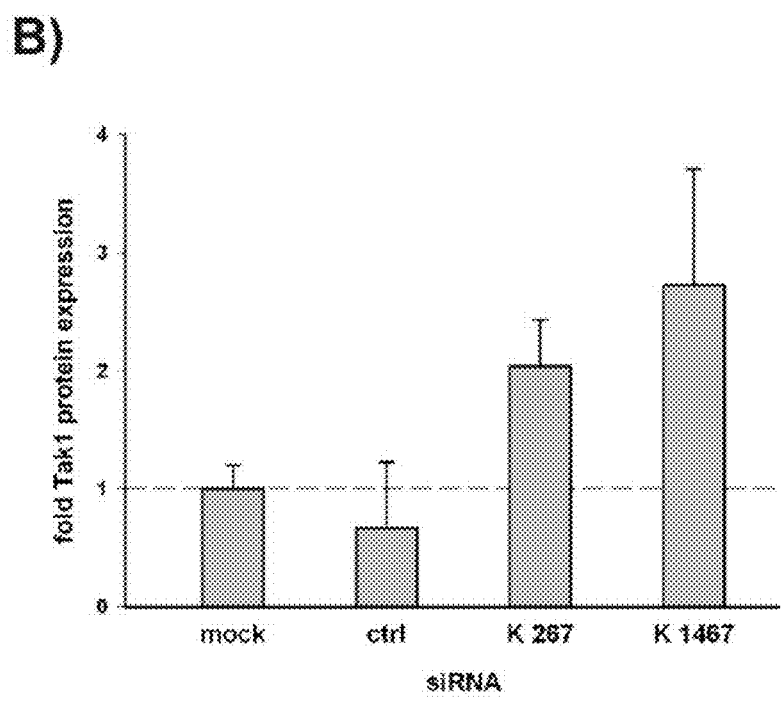
Figure 14 A, B

Figure 22:
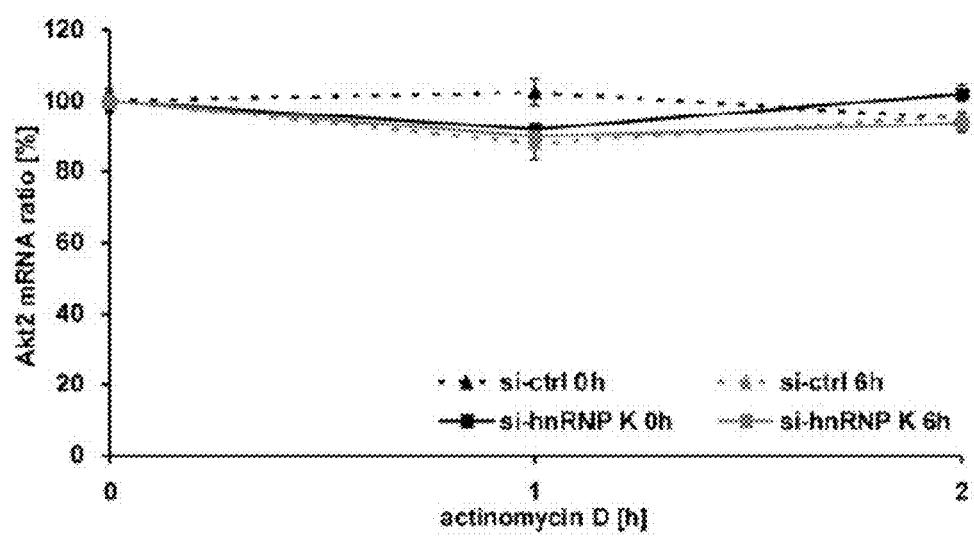

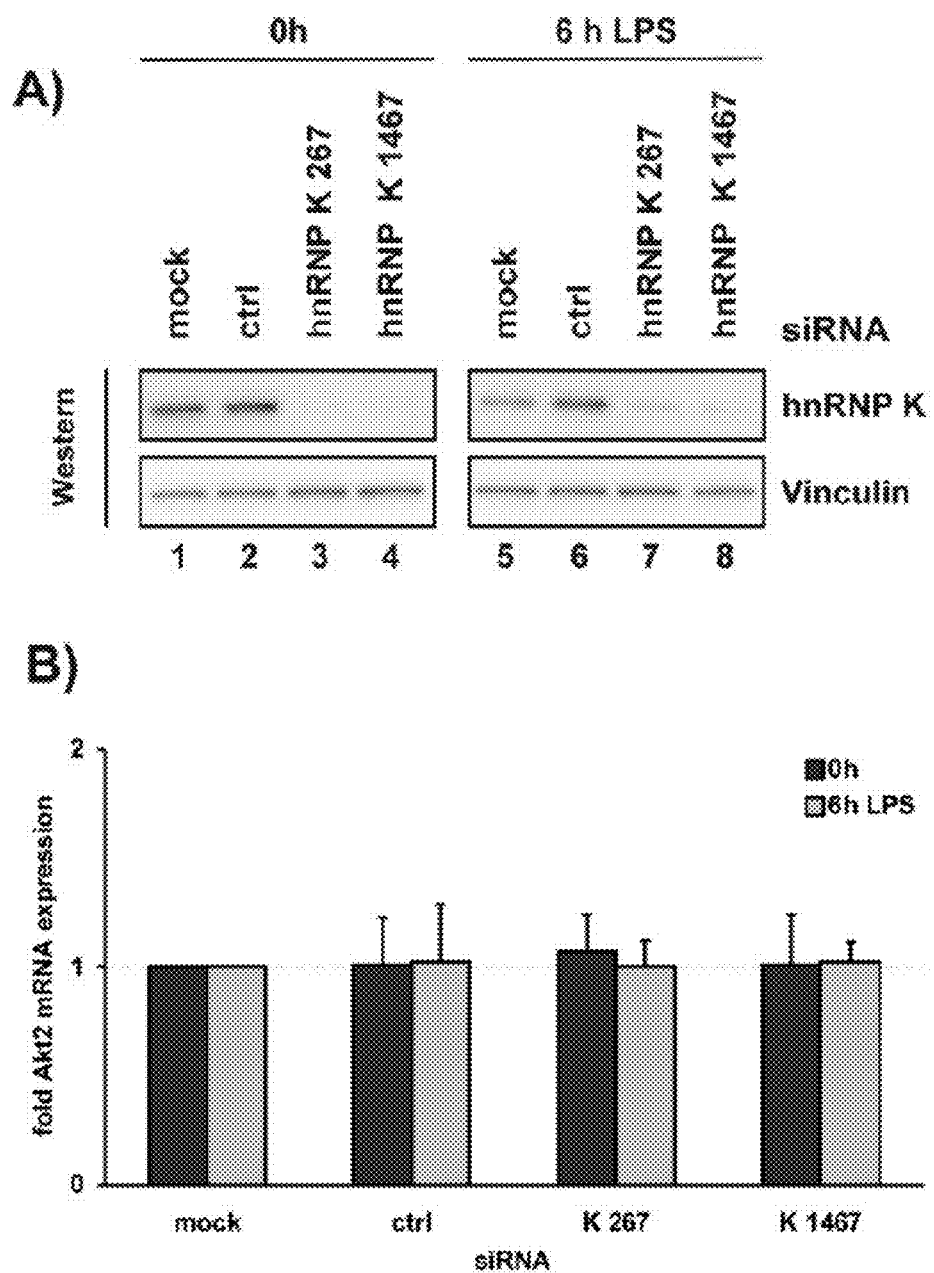
Figure 22 A, B

MODULATION OF TLR4-SIGNALING PATHWAY

The present invention relates to compounds for use in modulating the toll-like receptor 4 (TLR4) signaling pathway, as well as to a pharmaceutical composition comprising said compounds.

Innate immunity is the first line of defense against pathogens triggered by diverse microbial products. Inflammatory cells, such as macrophages, recognize invading microbial pathogens primarily through toll-like receptors (TLRs). TLR4 for instance recognizes lipopolysaccharide (LPS), which is a glycolipid located in the outer membrane of gram negative bacteria. In macrophages, LPS is transferred to the TLR4-MD2 complex by LPS-binding protein (LBP) and CD14. LPS binding induces the formation of a receptor multimer composed of two copies of the TLR4-MD2-LPS complex. TLR4 dimerization leads to the subsequent recruitment of the adapter proteins MyD88 (myeloid-differentiation primary-response gene 88) and TRIF (Toll/interleukin-1 receptor domain containing adaptor protein inducing interferon β). The latter mediates activation of interferon regulatory factor (IRF) 3 and IRF7, leading to enhanced expression of interferons, which activate members of the signal transducer and activator of transcription (STAT) family and induces a late NFκB response.

The MyD88-dependent pathway leads to the activation of the IκB kinase (IKK)-NFκB pathway (early response) and the three MAPK (mitogen activated kinases) pathways: ERK 1 and 2, c-Jun N-terminal kinase (JNK) and p38 (cf. Guha and Mackman (2001) *Cell. Signal.* 13, 85-94, wherein the LPS-dependent induction of gene expression is reviewed). MyD88 recruits IRAK1 and IRAK4. IRAK4 phosphorylates IRAK1, which mediates recruitment of tumor necrosis factor (TNF) receptor associated factor 6 (TRAF6) to the receptor complex. The IRAK1-TRAF6 complex dissociates from the TLR4-MD2 receptor to interact with and activate TAK1, a MAP3K member. TAK1, in turn, phosphorylates MKK4, MKK3/6 and IKK, which activates JNK and p38 pathways and induces IκB degradation, leading to NFκB activation. These signaling pathways activate a variety of transcription factors including NFκB and AP-1, which coordinate the induction of many genes encoding pro-inflammatory cytokines, such as TNFα, IL-1, IL-6, IL-8, high mobility group box-1 protein (HMGB-1) and macrophage migratory inhibitory factor (MIF) that are all critical mediators of septic shock (cf. FIG. 1 for an overview of the TLR4 signaling pathway).

Although the release of inflammatory mediators is essential to combat and to coordinate the cellular response to infection, excessive production of pro-inflammatory cytokines leads to systemic capillary leakage and vascular hemorrhage, tissue destruction, and ultimately lethal organ failure (cf. Hotchkiss and Karl (2003) *N. Engl. J. Med.* 348, 138-150, and Zanotti and Kumar (2002) *Expert Opin. Investig. Drugs* 11, 1061-1075, reviewing the pathophysiology of sepsis and septic shock, the function of cytokines in that process, as well as classical sepsis treatment). In order to dampen or terminate excessive production of pro-inflammatory cytokines in response to the pathogen exposure, macrophages also produce anti-inflammatory cytokines, like IL-10. Many cytokine mRNAs have very short half-lives. They bear AU-rich sequence elements (ARE) within their 3'-untranslated regions (UTRs) that represent protein binding sites. It has been shown that the LPS dependent MKK3/6-p38-MK2 pathway increases TNFα mRNA half-live through phosphorylation and stabilization of the specific ARE-binding protein tristetraprolin (TTP). Another example is the stabilization of the IL-8 mRNA by the ARE-binding protein KSRP.

Mechanisms that regulate the synthesis of TLR4 downstream kinases and their modulators, which is essential for tight control of inflammatory cytokine expression, are of particular scientific interest. These mechanisms include post-transcriptional processes. A role of trans-acting factors like RNA-binding proteins and microRNAs (miRNA) in the regulation of mRNAs that encode TLR4 downstream kinases and their modulators has begun to emerge, but information about the molecular mechanisms is scarce. Recently it has been shown that the RNA-binding protein AUF1 interacts with the TAK1 mRNA to promote its translation. Furthermore, miRNAs that recognize 3'UTR sites in mRNAs which encode signaling proteins have been identified. This has been shown for miR-146a and -146b, which control IRAK1 mRNA and TRAF6 mRNA translation, and miR-155, which modulates IL-1 signaling of LPS-activated monocyte-derived dendritic cells.

Besides the systemic inflammatory response syndrome (SIRS), sepsis is a major cause of mortality in intensive care practice. In sepsis, the symptoms of SIRS are present in combination with a bacterial infection. The various complications related to sepsis, which lead to septic shock and multi-organ failure, are caused by an over-excessive immune response.

In conventional therapies of sepsis-related inflammation, antibiotics and glucocorticoids are used systemically, which can reduce the release of cytokines, such as TNFα and various interleukins, and, therefore, control the immune response. However, the use of antibiotics can lead to an uncontrolled release of LPS and other pathogenic compounds of the outer membrane of inactivated gram negative bacteria, resulting in an overshooting immune reaction due to an increased activation of TLR4 receptors. These therapies are usually combined with a broad spectrum of organ-specific measures. However, a specific control of cytokine production and release by monocytes and macrophages, and thus a control of the inflammation reaction leading to sepsis, by specific interventions into TLR4-dependent signaling pathways has so far not been possible.

Therefore, the technical problem underlying the present invention is to provide compounds useful in modulating the TLR4 signaling pathway and thus controlling the inflammatory process.

The solution to the above technical problem is achieved by the embodiments characterized in the claims.

In particular, the present invention is based on the finding that specific mRNA-protein complexes (ribonucleoprotein complexes; mRNP) mediate post-transcriptional regulation of mRNA stability and translation. Both mechanisms, which allow a fast reaction to extracellular stimuli such as LPS, could be important determinants for the synthesis of kinases and modulators of the TLR4 signaling pathway.

The characterization of regulatory mRNPs has lead to the identification of regulatory molecular interactions, which allowed a biochemical interference with the synthesis of pro- and anti-inflammatory cytokines and, thus, the development of therapeutically active agents for the specific control of inflammatory reactions.

The present invention allows a specific therapy based on the reduction of LPS-induced TLR4 signaling pathway activity. In particular, the synthesis and release of cytokines can be modulated and an over-excessive immune reaction, which can lead to sepsis, is dampened.

In particular, in the present invention, mRNAs binding to heterogeneous nuclear ribonucleoprotein K (hnRNP K) in an LPS-dependent manner have been isolated from macrophages by affinity chromatography. Further, hnRNP K has been characterized as a regulator of mRNA translation in eukaryotic cells. Recently, hnRNP K could be identified as a potential modulator of LPS-dependent translation of mRNA coding for key components of the TRL4 signaling pathway such as IRAK4, TAK1, IRAK1BP1, Erc1/ELKS, CARM1/PRMT4, PIK3ca and Akt3.

The function of hnRNP K as a translational inhibitor is modulated by post-translational modifications, i.e. serine and tyrosine phosphorylation and asymmetric arginine methylation. The cytoplasmatic accumulation of hnRNP K that determines its function in the control of mRNA translation is driven by ERK-dependent phosphorylation on S284, S353. Furthermore, hnRNP K specifically activates the tyrosine kinase c-Src and becomes a substrate of that kinase. C-Src dependent phosphorylation of tyrosine 458 (Y458) in the hnRNP K homology (KH) domain 3 of hnRNP K leads to the loss of RNA-binding activity and consequently its role as an inhibitor of mRNA translation in vitro. The asymmetric dimethylation of hnRNP K by protein arginine methyltransferase 1 (PRMT1) at five specific arginine residues (R256, R258, R268, R296, R299) controls the activation of c-Src by hnRNP K in transfected cells.

Accordingly, in a first aspect the present invention relates to a compound for use in modulating the toll-like receptor 4 (TLR4) signaling pathway, wherein said compound modulates the binding of heterogeneous nuclear ribonucleoprotein K (hnRNP K) to mRNA.

Herein, the term "compound" is not specifically limited and includes any chemical compound or mixture of compounds which is effective in modulating the binding of hnRNP K to mRNA. The compound of the present invention includes organic or inorganic chemical compounds as well as biochemical compounds, such as peptides, proteins, nucleic acids, and combinations thereof. Further, the term "compound" includes any compounds that interfere with interactions that mediate the function of hnRNP K as modulator of target mRNA translation and/or stability. Those interactions can be direct interactions between hnRNP K and the mRNA, or indirect interactions, i.e. interactions mediated by other components of the hnRNP K mRNP, including proteins and nucleic acids. Accordingly, said interactions include not only interactions between or with proteins, peptides, and amino acids, but also interactions between or with nucleic acids, oligonucleotides and nucleotides. These interactions can be modulated e.g. by post-transcriptional modifications of amino acids and/or covalent modifications of nucleotides in both DNA and RNA molecules, which modifications are catalyzed enzymatically.

Moreover, the terms "modulating" or "modulates" as used herein refer to positive as well as negative regulation, i.e. an up-regulation or a down-regulation.

Further, the term "binding" used herein is not specifically restricted and includes any mode of chemical or physical attractive interaction, such as covalent binding, binding via hydrogen bridges, and binding via van-der-Waals forces.

According to one example of the above-defined compound, said mRNA at least codes for a protein selected from IRAK4, TAK1, IRAK1BP1, Erc1/ELKS, CARM1/PRMT4, PIK3ca and Akt3, or a fragment or a derivative of said proteins.

Herein, the term "derivative" is not specifically restricted and includes any chemical modification of the above-defined proteins.

In a particular example of the present invention, the compound modulates the binding of hnRNP K to mRNA by hnRNP K competition. Respective compounds are not particularly limited and can be selected from the group consisting of nucleic acids, DNA oligonucleotides, RNA oligonucleotides, small interfering RNAs (siRNAs), short hairpin RNAs (shRNAs), aptamers, peptides, antibodies, antibody fragments, and fragments of proteins that are processed by cellular proteases, wherein peptides, in particular small peptides (e.g. peptides having at most 100, at most 90, at most 80, at most 70, or less amino acid residues), and nucleic acids, in particular small nucleic acids (e.g. nucleic acids having at most 50, at most 40, at most 30, or less nucleotides), in particular RNA oligonucleotides, are especially preferred. In a specific embodiment, the compound that modulates the binding of hnRNP K to mRNA by hnRNP K competition is the 79 amino acids peptide KH3 (SEQ ID NO: 1) which corresponds to the third hnRNP K homology domain of hnRNP K. In another specific embodiment, the compound that modulates the binding of hnRNP K to mRNA by hnRNP K competition is the 38 nucleotides long RNA oligonucleotide 2R (SEQ ID NO: 2) which is a short fragment of the differentiation control element (DICE) found in the 3' untranslated region (3'UTR) of reticulocyte 15-lipoxygenase mRNA. In this context, stable peptides with so far unknown functions can be detected for hnRNP K, which peptides are processed by specific proteases in different cell types, e.g. monocytes.

In another particular example of the present invention, the compound modulates the binding of hnRNP K to mRNA by modulating ERK-dependent phosphorylation of hnRNP K, and/or by modulating cSrc-dependent phosphorylation of hnRNP K. Respective compounds are not particularly limited and can be selected from the group consisting of siRNAs, shRNAs, antibodies, antibody fragments, enzymes, kinase inhibitors, and specifically modified (e.g. phosphorylatable) peptides. In this context, modified peptides can compete with hnRNP K for ERK- and/or cSrc-dependent phosphorylation.

In another particular example of the present invention, the compound modulates the binding of hnRNP K to mRNA by modulating PRMT1-dependent methylation of hnRNP K. Respective compounds are not particularly limited and can be selected from the group consisting of siRNAs, shRNAs, antibodies, antibody fragments, and enzymes, inhibitory molecules, and specifically modified (e.g. asymmetrically methylatable) peptides. In this context, modified peptides can compete with hnRNP K for PRMT1-dependent methylation.

In another particular example of the present invention, the compound modulates the binding of hnRNP K to mRNA by modulating protein-protein interactions within the hnRNP K complex. Respective compounds are not particularly limited and can be selected from the group consisting of peptides, antibodies, antibody fragments, aptamers, and oligonucleotides, in particular CU-rich oligonucleotides. In this context, CU-rich oligonucleotides bind to the third KH-domain of hnRNP K and can be used to compete binding to mRNA or nucleic acid-protein interactions in general.

Suitable nucleic acids, DNA oligonucleotides, RNA oligonucleotides, small interfering RNAs (siRNAs), short hairpin RNAs (shRNAs), aptamers, peptides, antibodies, antibody fragments, enzymes, kinase inhibitors, inhibitory molecules, as defined above are not particularly limited, provided they are capable of performing the functions as defined above. As a particular example, as an inhibitor of ERK-dependent phosphorylation of hnRNP K (2-(2-amino- 3-methoxyphenyl)-4H-1-benzopyran-4-one (PD98059) may be used. Further, specific tyrosine kinase or serine kinase inhibitors may be used to interfere with hnRNP K phosphorylation by either c-Src or ERK1/2.

In a second aspect, the present invention relates to a pharmaceutical composition, comprising at least the above-defined compound according to the present invention.

In a further embodiment, the above-defined pharmaceutical composition further comprises at least one pharmaceutically acceptable solvent, diluent and/or excipient.

The pharmaceutical composition defined above may be administered by any route known in the art, including for example oral, parenteral (such as intravenous, intra-arterial or intramuscular), topical and rectal administration.

Pharmaceutically acceptable solvents, diluents and excipients that can be used in the pharmaceutical composition of the present invention are not particularly limited and are known in the art.

In a further aspect, the present invention relates to a compound of the present invention which is further for use in the therapeutic treatment of sepsis.

Moreover, a further aspect the present invention relates to a method for the therapeutic treatment of sepsis, comprising the step of administering a compound of the present invention to a patient in need thereof.

Figure 1:
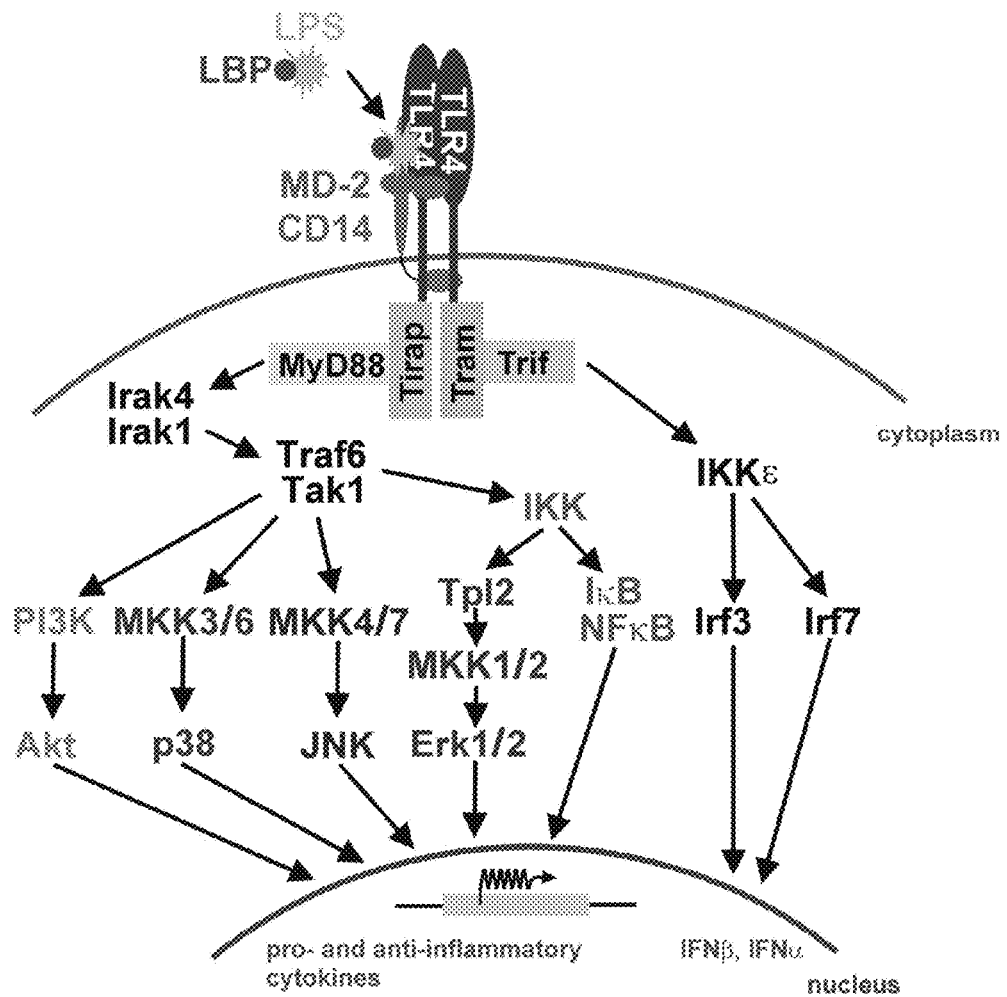

The figures show:

FIG. 1: Overview of the TLR4 signaling pathway

Schematic representation of the TLR4 signaling pathway.

Figure 2:
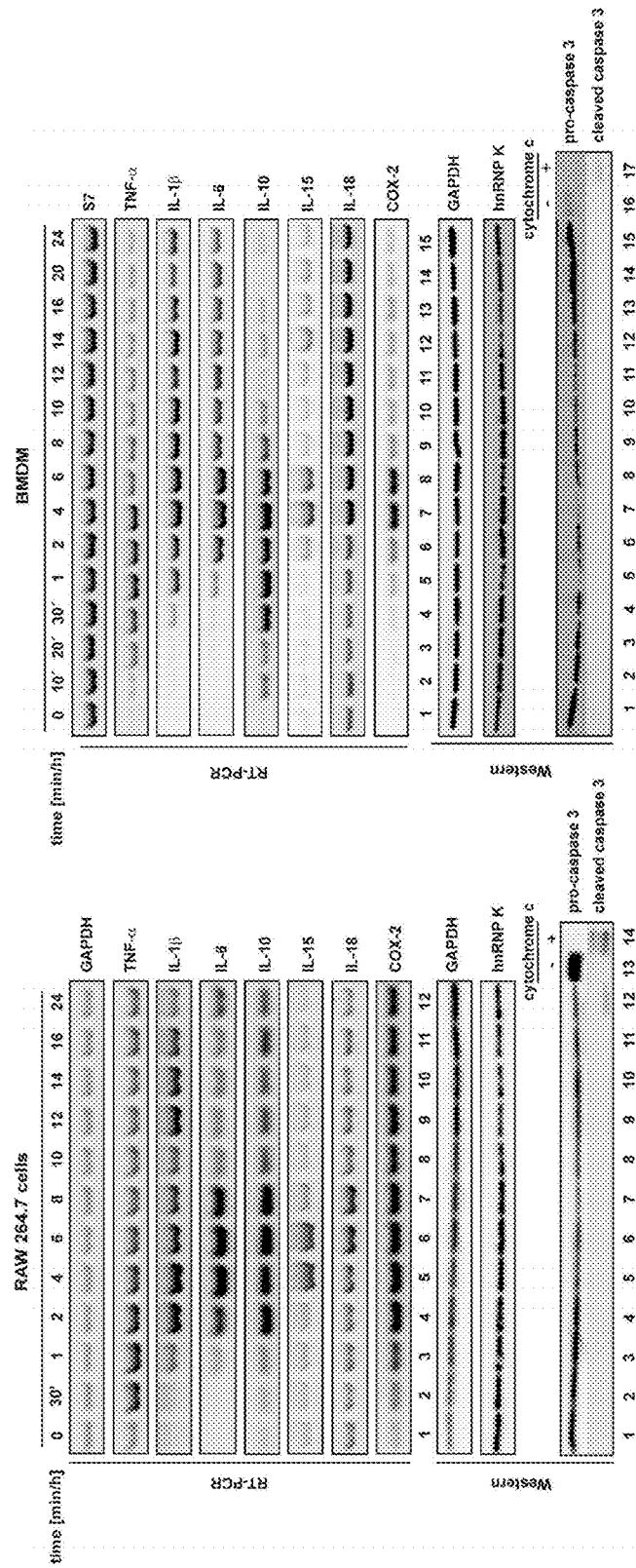

FIG. 2: Time-dependent activation of macrophages by LPS

Raw 264.7 cells (upper panel) and BMDM (lower panel) were treated with 10 ng/ml and 80 ng/ml LPS, respectively. mRNA synthesis of pro-inflammatory cytokines (TNF-α, IL-1β, IL-6, IL-15, and IL-18), the anti-inflammatory cytokine IL-10 and Cox-2 as well as GAPDH or S7 was monitored by RT-PCR. Protein expression of hnRNP K and GAPDH was not affected by LPS stimulation. Cleaved caspase-3 was only detectable after 24 h, indicating that the cells did not undergo apoptosis at earlier time points.

Figure 3:
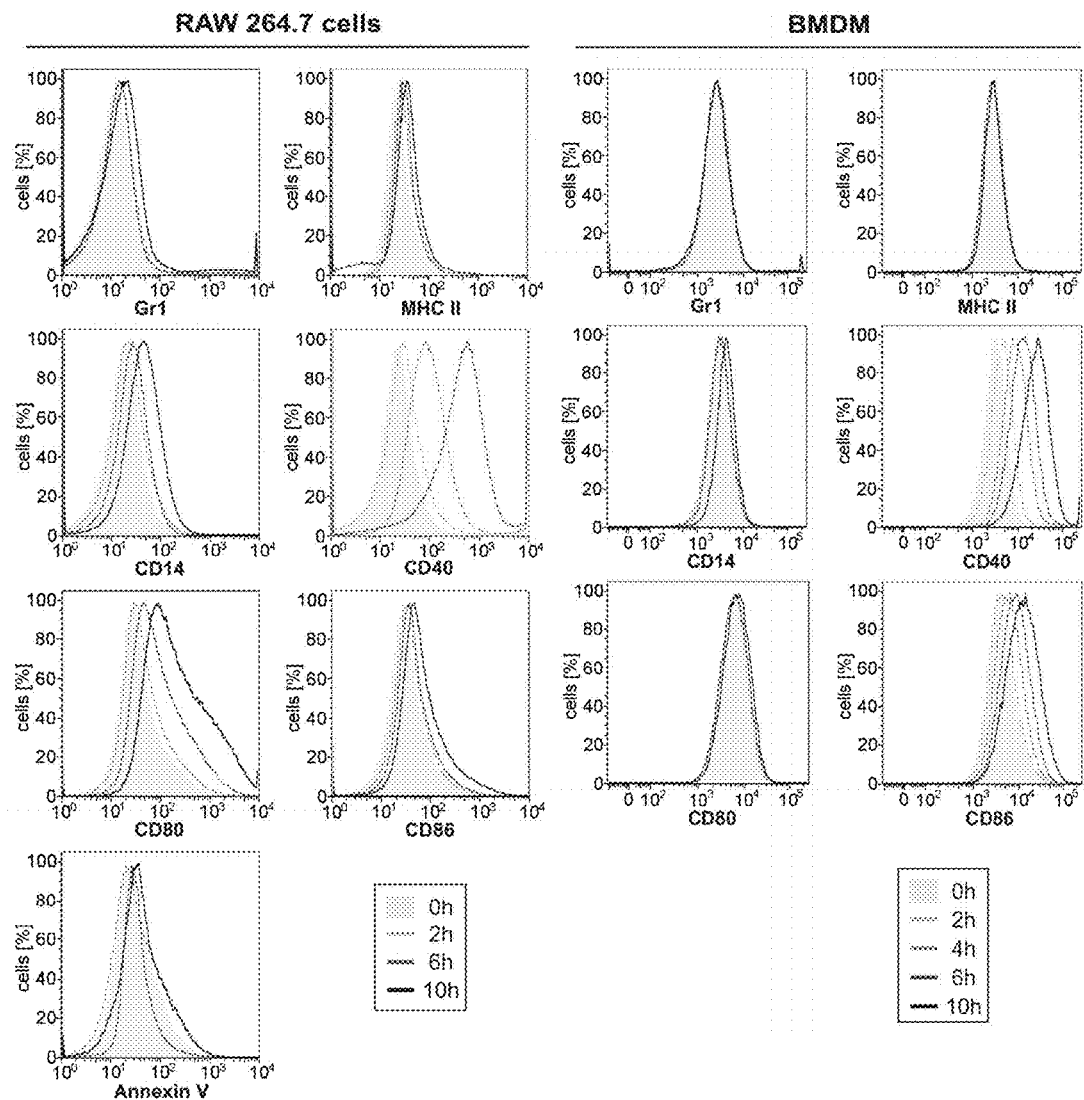

FIG. 3: Flow cytometric analysis of LPS-activated macrophages

To further characterize the activation of macrophages, flow cytometric analysis of Raw 264.7 cells (left panel) and BMDM (right panel) was performed. Living cells were analyzed for the expression of specific macrophage markers (CD11b, CD115, F4/80). Positive cells showed increased expression of activation markers Gr1, MHCII, CD14, CD40, CD80 and CD86 compared to untreated cells. Annexin V staining was used to detect apoptosis.

Figure 4:
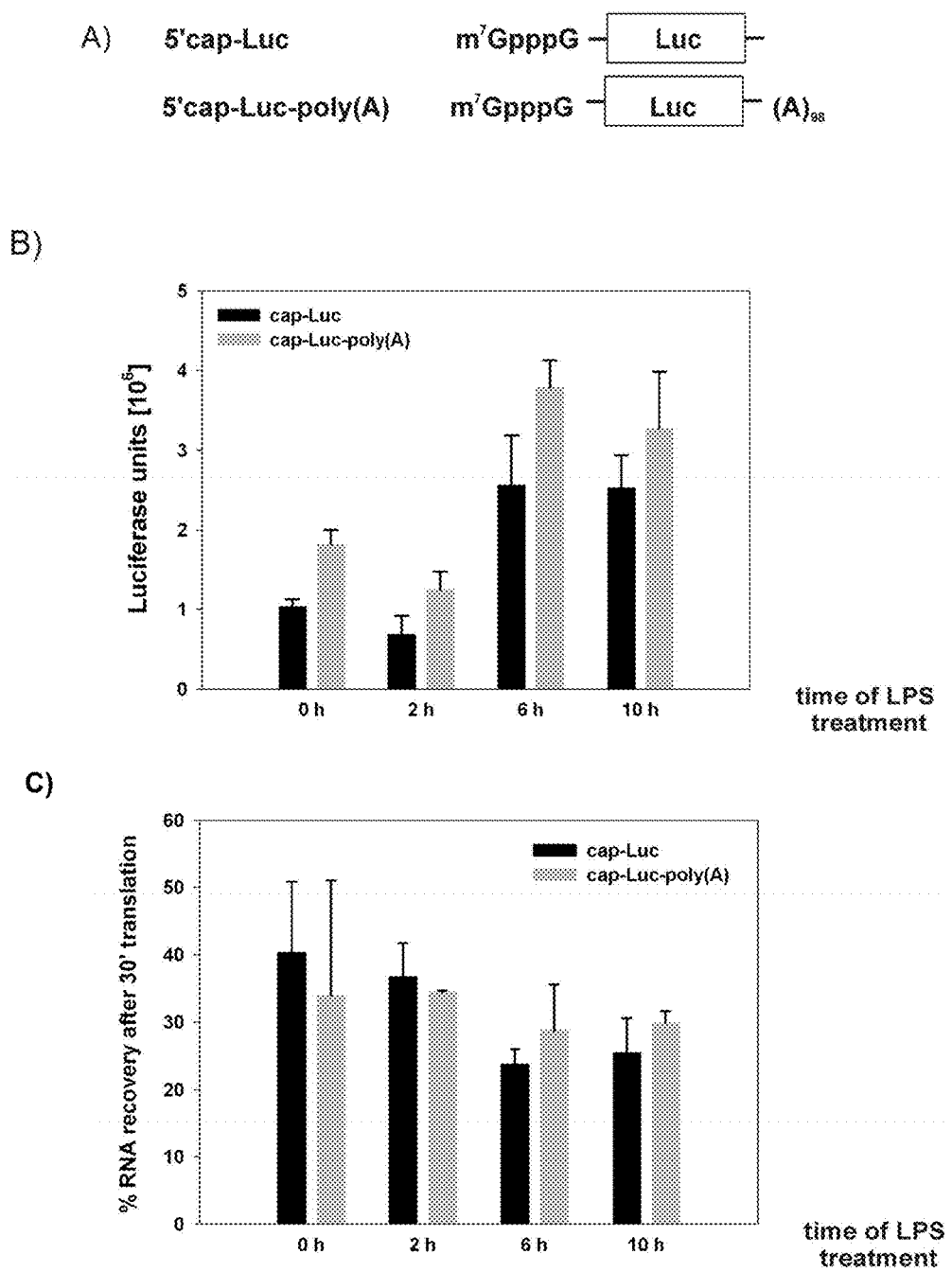

FIG. 4: mRNA translation is enhanced after LPS treatment in vitro

Cytoplasmic extracts were prepared from untreated Raw 264.7 cells and after LPS stimulation. Translation activity was monitored using Luciferase (Luc) reporter constructs bearing a 5'm7G-cap and a poly(A) tail (A). An increase in Luc activity in extracts prepared from cells treated with LPS for 6 h and 10 h compared to untreated cells was observed (B). Reporter mRNAs were extracted from translation reactions and mRNA stability was measured by qRT-PCR, showing that enhanced Luc activity was not a result of increased mRNA stability (C).

Figure 5:
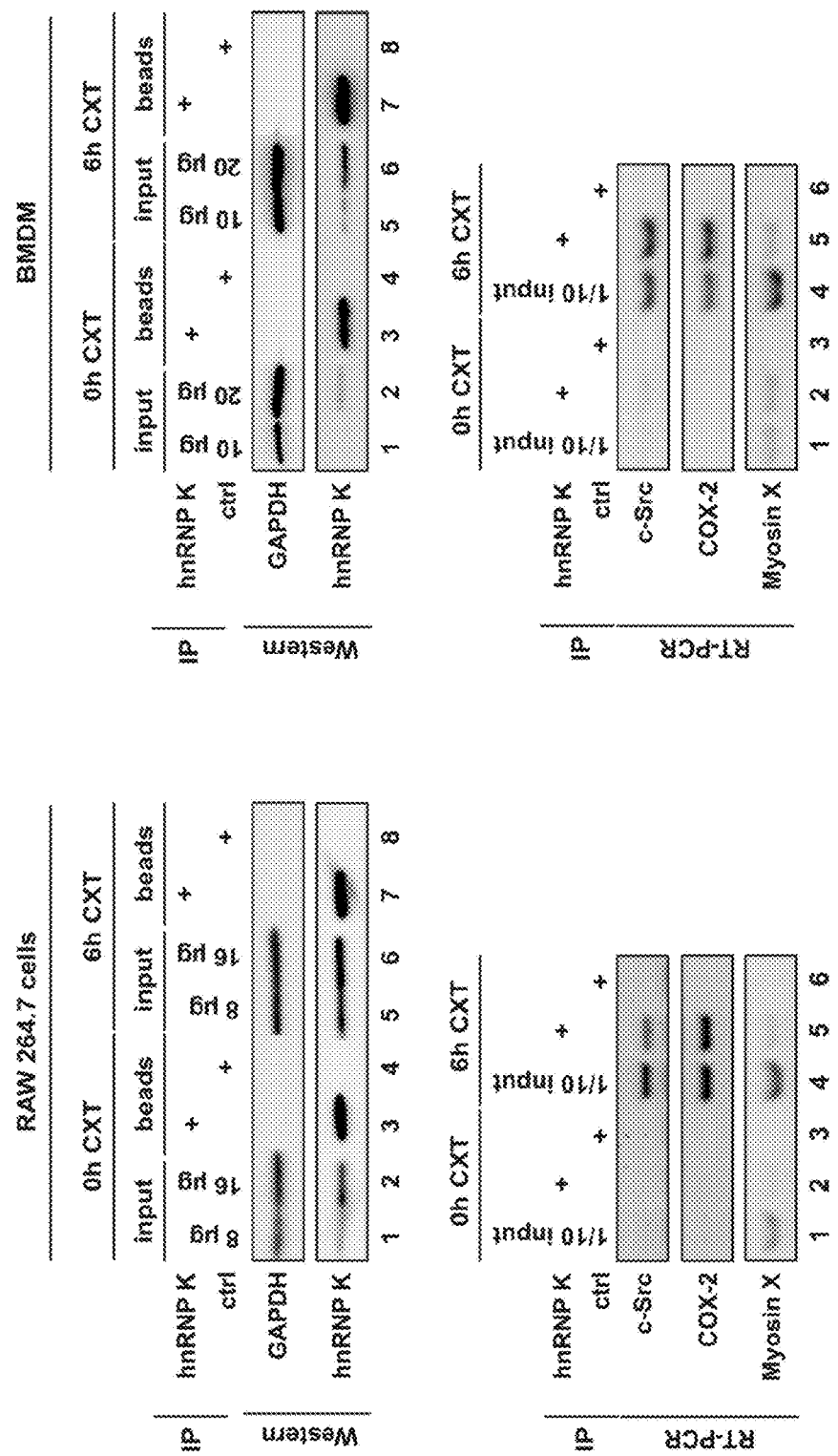

FIG. 5: HnRNP K interacts with c-Src and COX-2 mRNA in extracts of RAW 264.7 cells and BMDM.

Upper panel: Immunoprecipitated hnRNP K from cytoplasmic extracts (CXT) of untreated RAW 264.7 cells (left) and BMDM (right) and after 6 h LPS stimulation was detected by Western blotting. For the control immunoprecipitation a non-related antibody (ctrl) was used.

Lower panel: Coprecipitated mRNAs were detected by RT-PCR as indicated.

Figure 6:
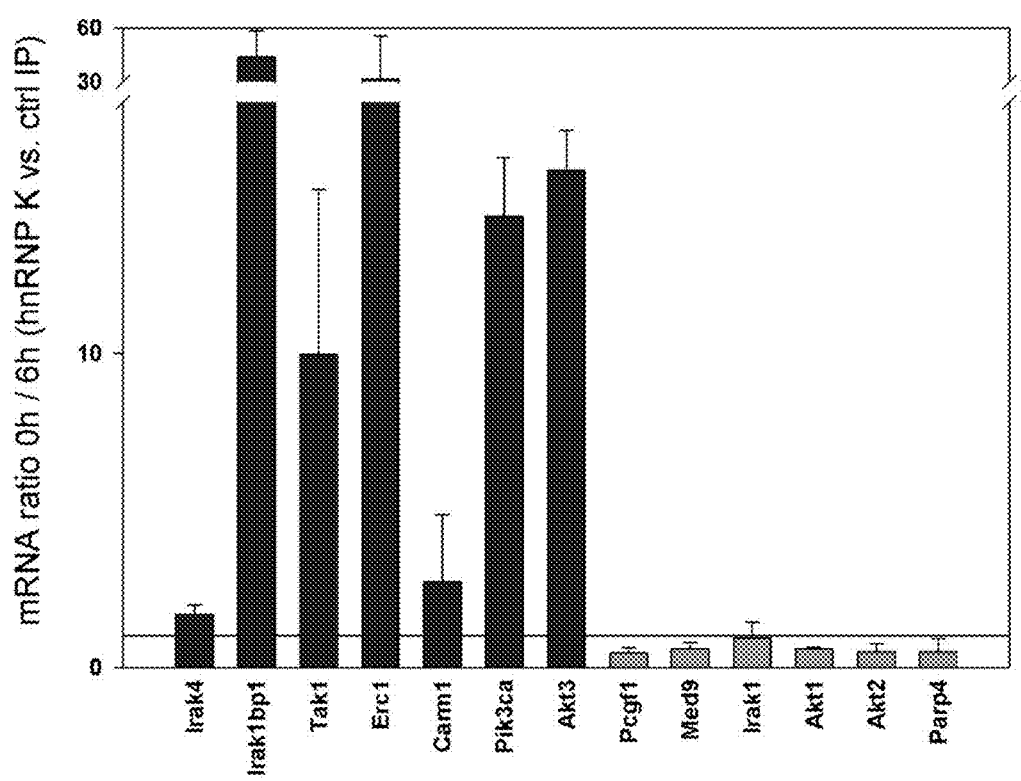

FIG. 6: Verification of LPS-mediated differential interaction of specific mRNAs with hnRNP K by qRT-PCR.

Equal amounts of CXT were used for immunoprecipitation with an anti-hnRNP K and a control antibody. Copurified mRNAs were analyzed by qRT-PCR. mRNAs specifically enriched on hnRNP K were normalized to five controls that did not interact with hnRNP K. Specific binding in untreated cells was compared to 6 h LPS treatment (higher values represent stronger mRNA binding in untreated cells).

Figure 7:
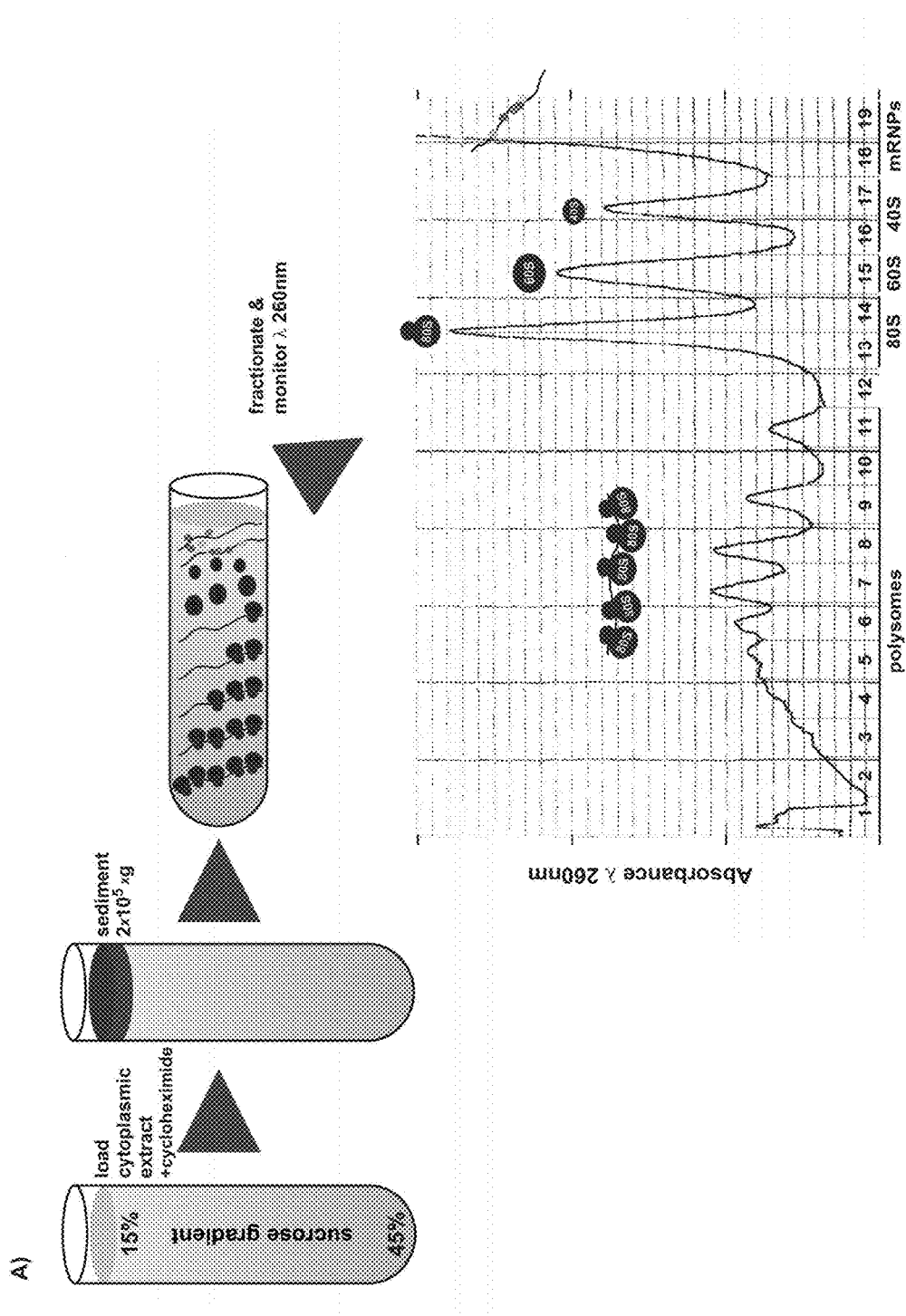
Figure 7:
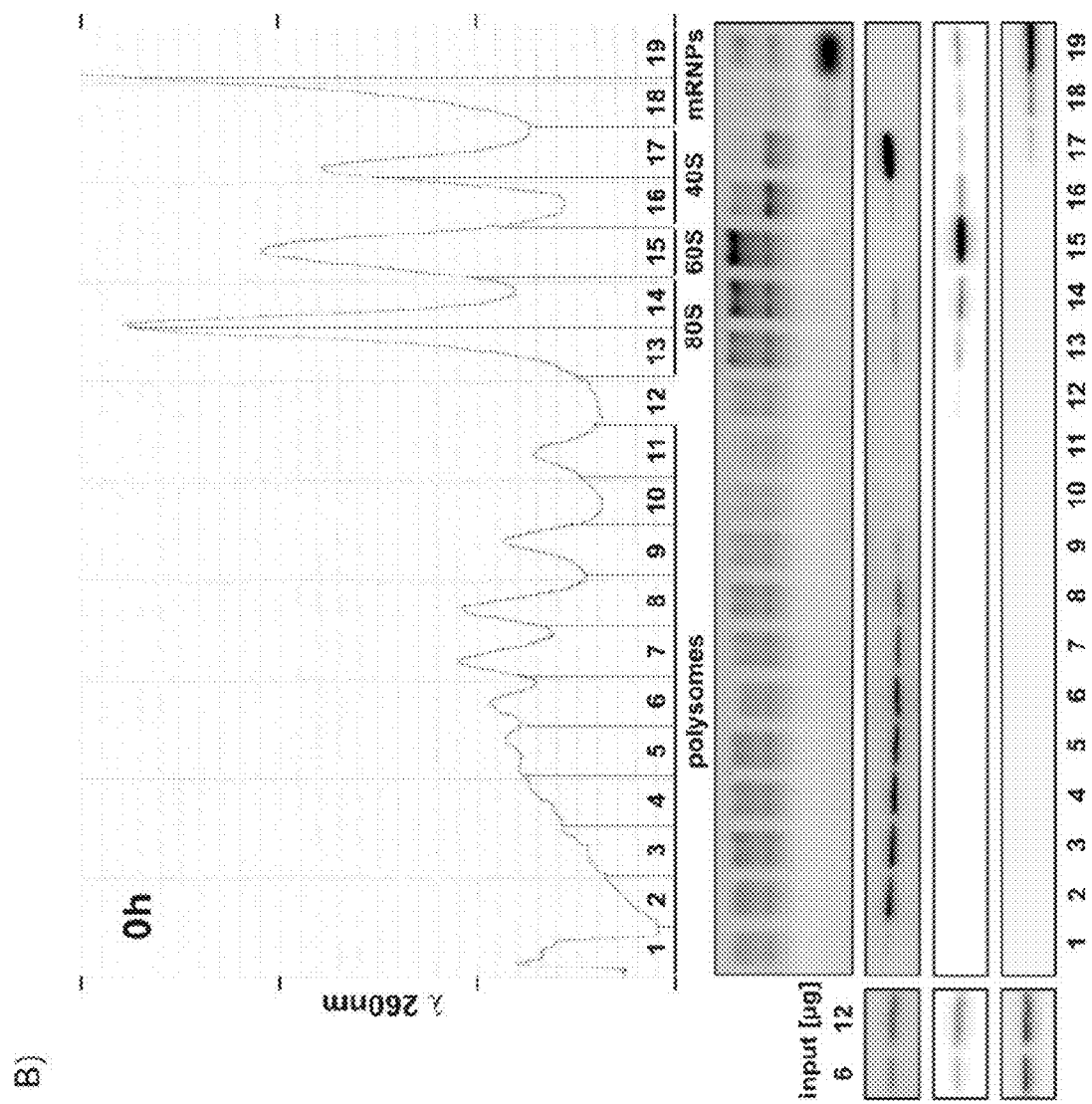
Figure 7:
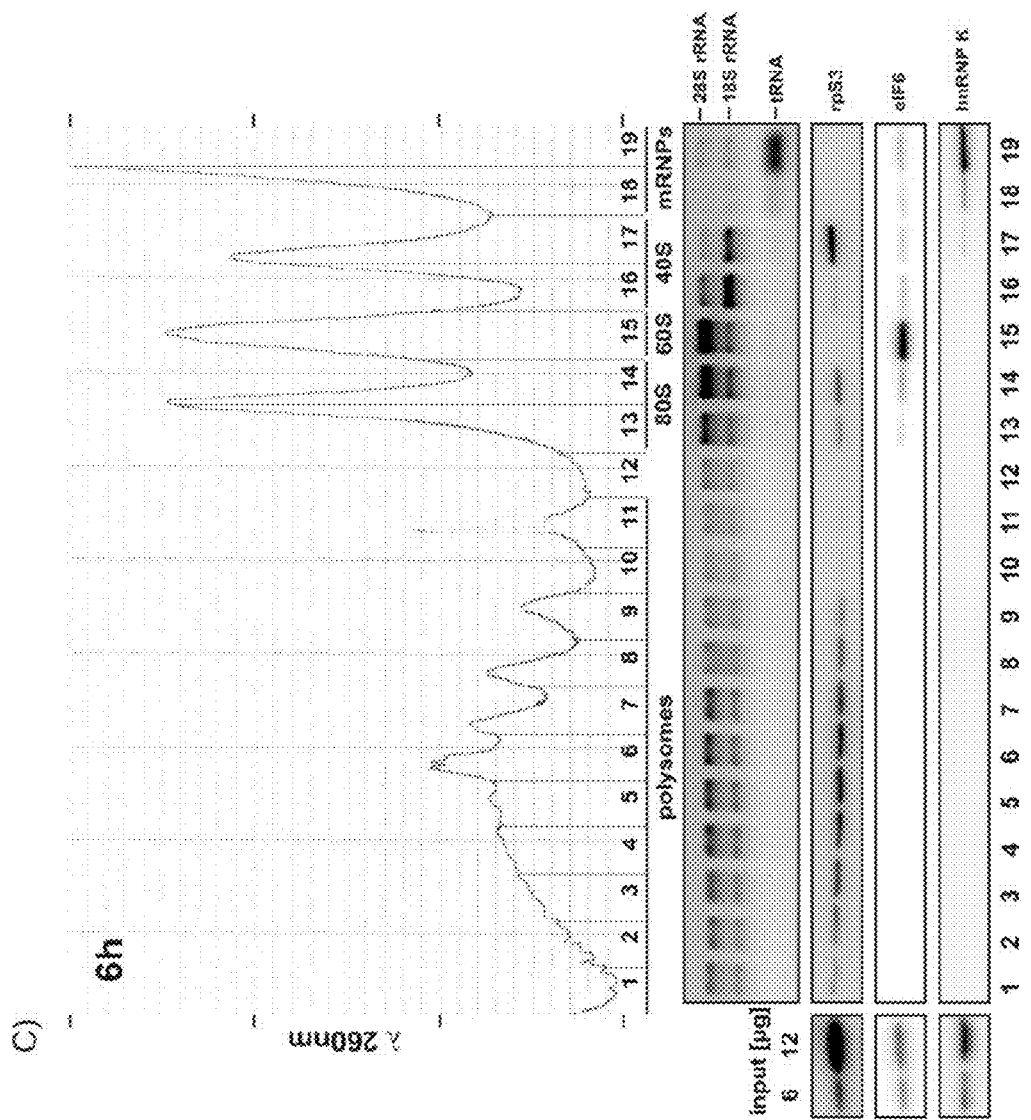

FIG. 7: hnRNP K sediments to mRNP fractions in extracts of untreated and LPS stimulated RAW 264.7 cells.

(A) Schematic representation of the experiment. Sucrose gradient profiles of CXTs of untreated RAW 264.7 cells (B) and after 6 h LPS stimulation (C) in the presence of cycloheximide. RNA was extracted from gradient fractions and the distribution of 18S and 28S rRNA was analyzed. The distribution of rpS3, eIF6 and hnRNP K was determined by Western blotting.

Figure 8:
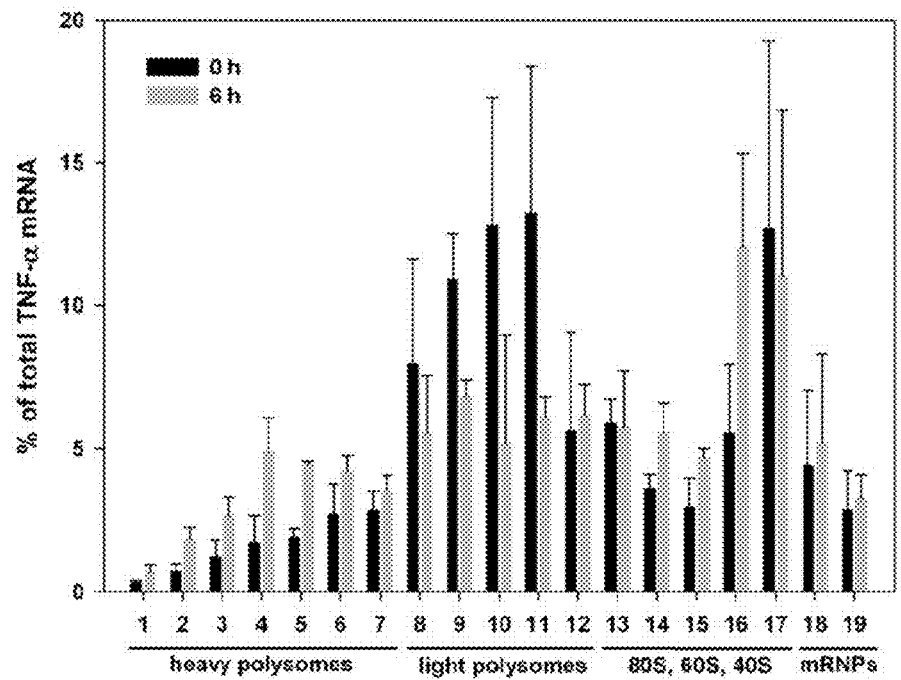
Figure 8:
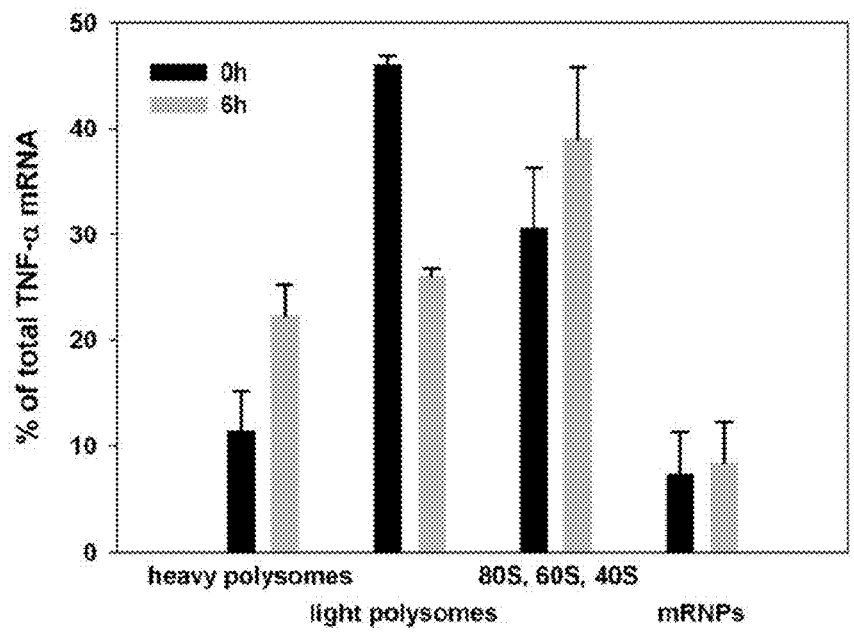

FIG. 8: TNFα mRNA sediments to heavy polysomes in LPS stimulated RAW 264.7 cell extracts.

(A) Distribution of TNFα mRNA in sucrose gradient fractions from untreated RAW 264.7 cells and after 6 h LPS stimulation.

(B) Cumulative distribution of TNFα mRNA to heavy and light polysomes, initiating ribosomes and mRNPs as indicated in (A).

The compound as a well as the pharmaceutical composition of the present invention allow for the effective modulation of the TLR4-signaling pathway, particularly by modulating the binding of hnRNP K to mRNA. Such a modulation advantageously enables to specifically control the release e.g. of cytokines, without completely blocking the entire TLR4 signaling pathway. As a consequence, complications connected to severe inflammatory processes, such as sepsis, can effectively be reduced or avoided.

Figure 9:
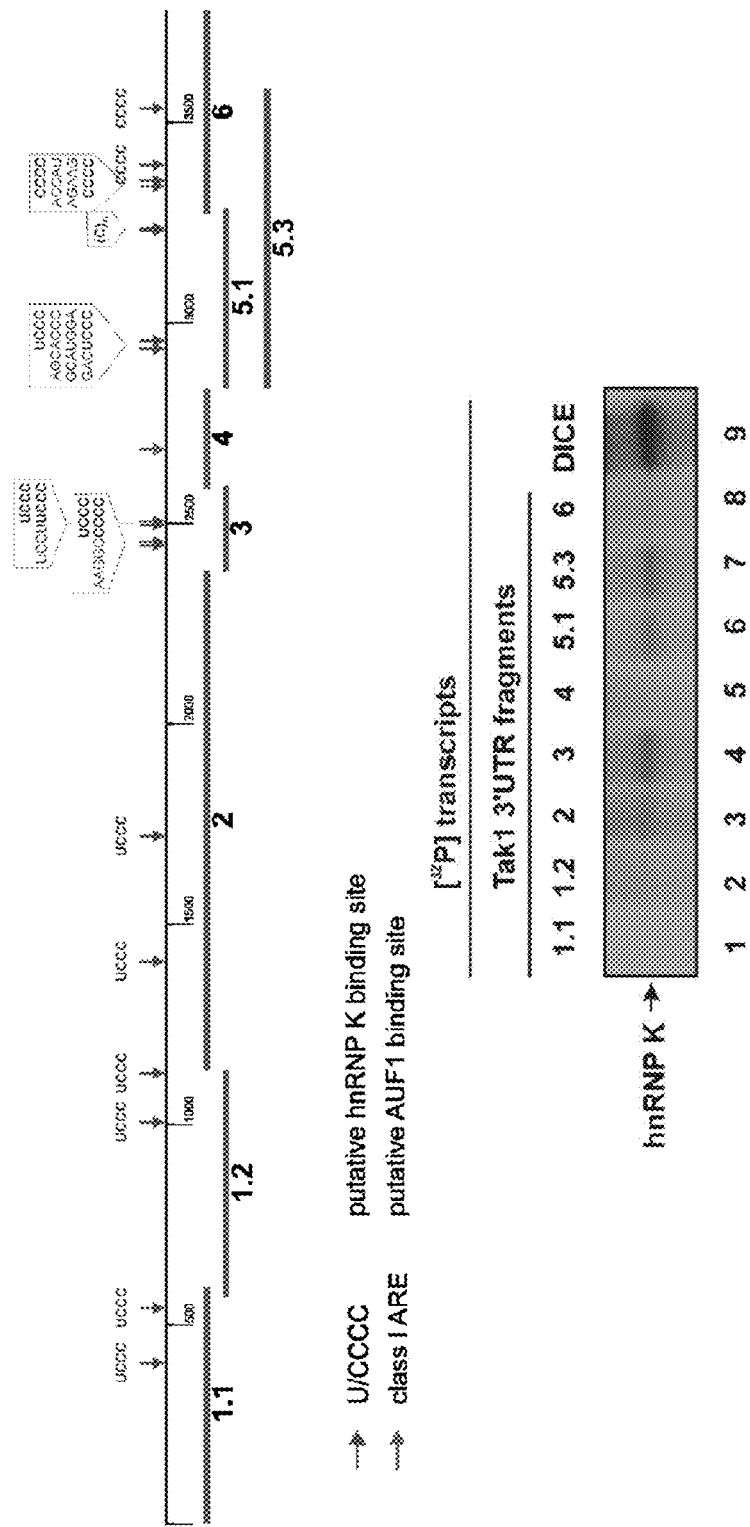

FIG. 9: HnRNP K directly binds to the TAK1 mRNA 3'UTR.

Upper panel: schematic representation of the TAK1 mRNA 3'UTR. Lower panel: 14.5 fmol [$^{32}$P]-labeled TAK1 mRNA 3'UTR fragments (lanes 1-8) and the r15-LOX mRNA 3'UTR DICE (lane 9) were incubated with 7.2 pmol recombinant hnRNP K as indicated and subjected to UV-crosslinking.

Figure 10:
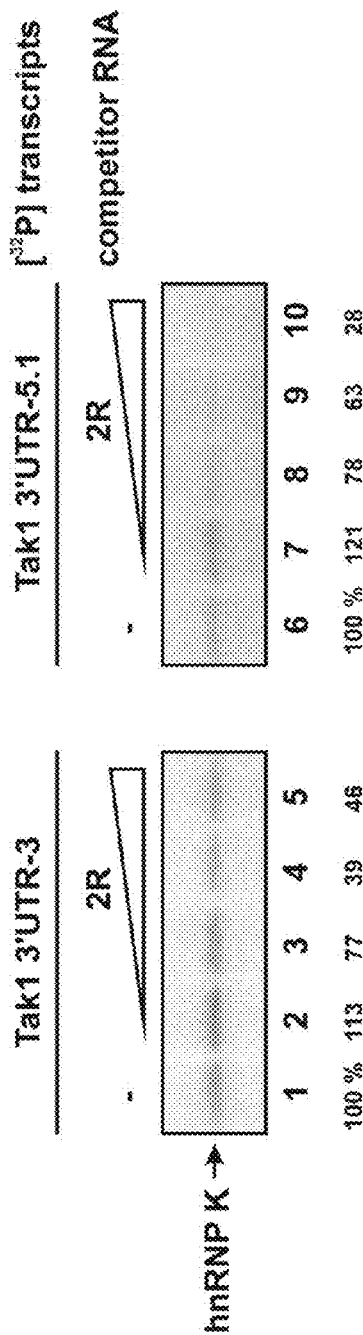

FIG. 10: 2R competes hnRNP K binding to TAK1 mRNA 3'UTR fragments 3 and 5.1.

40 fmol [$^{32}$P]-labeled TAK1 mRNA 3'UTR fragment 3 (lanes 1-5) or 5.1 (lanes 6-10) was incubated with 7.2 pmol hnRNP K (lanes 1-10) in the presence of 10, 50, 100 or 200 fold molar excess of unlabeled competitor RNA 2R (lanes 2-5 and 7-10).

Figure 11:
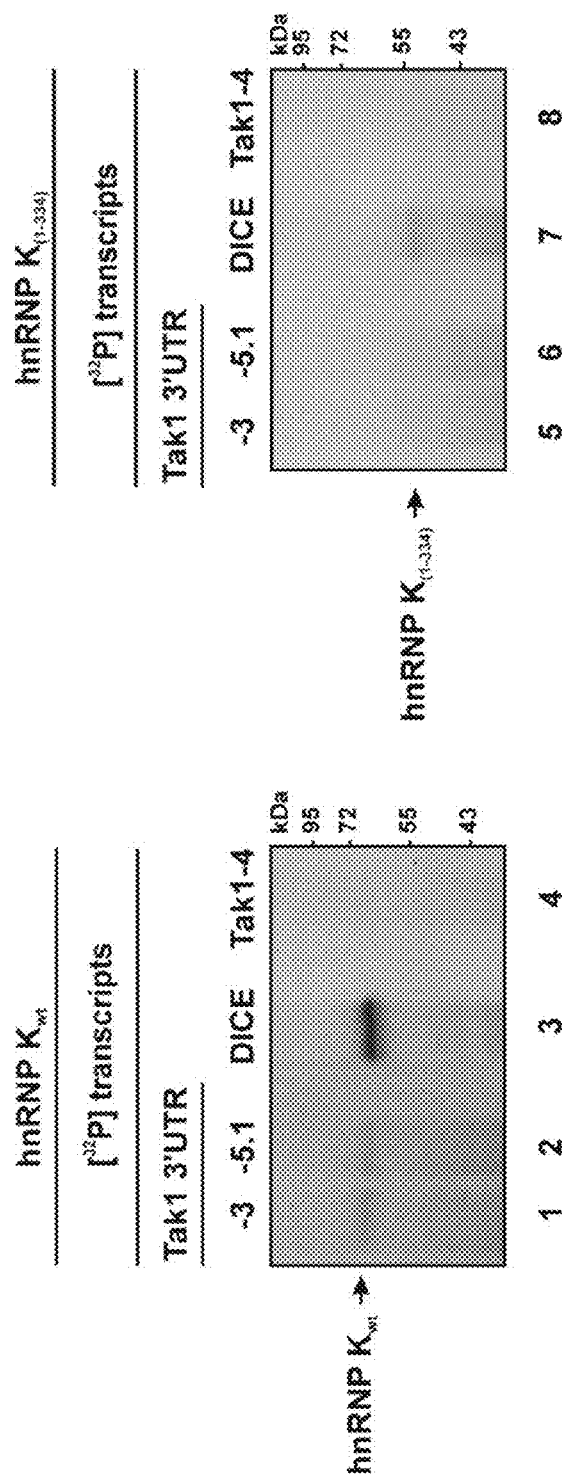

FIG. 11: HnRNP $K_{(1-334)}$ does not interact with TAK1 mRNA 3'UTR fragments 3 and 5.1.

40 fmol [$^{32}$P]-labeled TAK1 mRNA 3'UTR fragments 3 (lanes 1 and 5), 5.1 (lanes 2 and 6), r15-LOX mRNA 3'UTR DICE (lanes 3 and 7) or TAK1 mRNA 3'UTR fragment 4 (lanes 4 and 8) were incubated with 7.2 pmol recombinant His-hnRNP $K_{wt}$ (lanes 1-4) or His-hnRNP $K_{(1-334)}$ (lanes 5-8), as indicated and subjected to UV-crosslinking.

Figure 12:
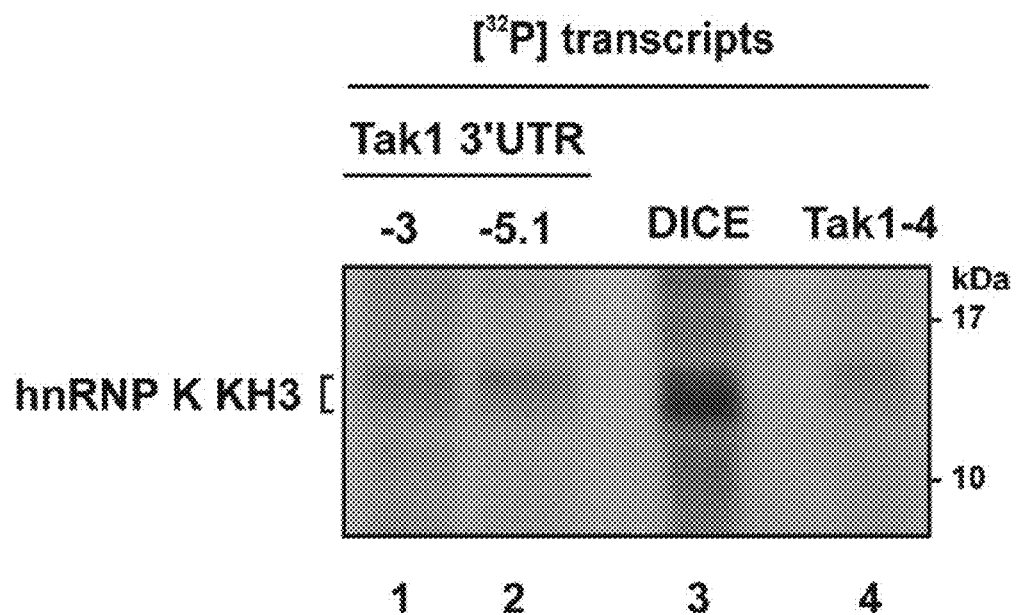

FIG. 12: KH3 of hnRNP K interacts with the TAK1 mRNA 3'UTR.

40 fmol [$^{32}$P]-labeled TAK1 mRNA 3'UTR fragments 3 (lane 1) and 5.1 (lane 2), r15-LOX mRNA 3'UTR DICE (lane 3) or TAK1 mRNA 3'UTR fragment 4 (lane 4) were incubated with 530 pmol recombinant KH3.

Figure 13:
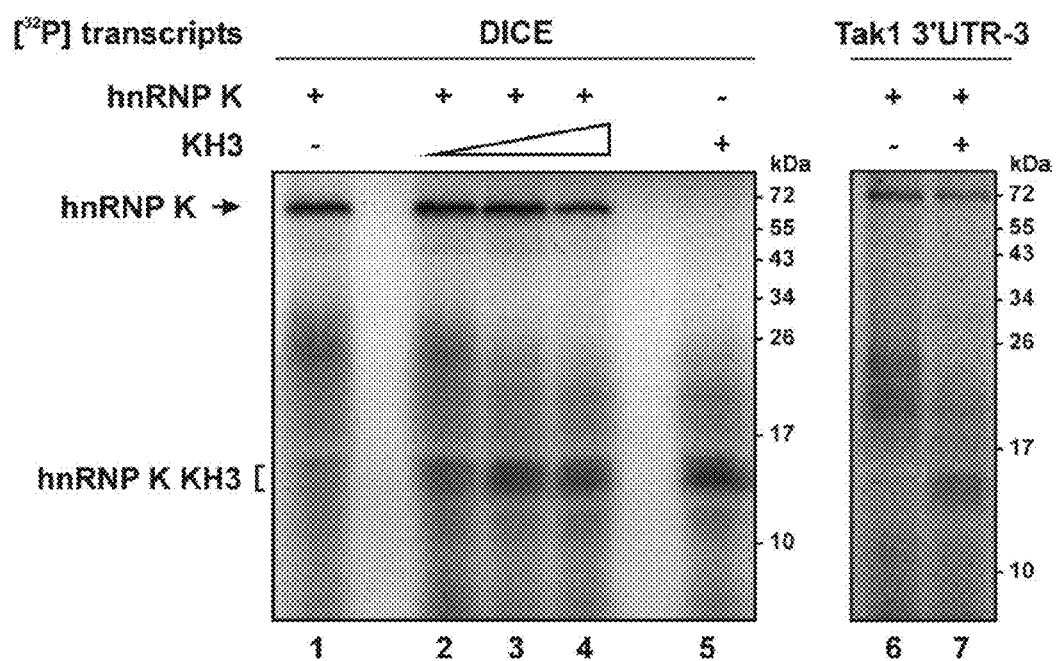

FIG. 13: KH3 competes for binding of full-length hnRNP K with the r15-LOX mRNA 3'UTR DICE and TAK1 mRNA 3'UTR fragment 3.

40 fmol [$^{32}$P]-labeled r15-LOX mRNA 3'UTR DICE (lanes 1-5) was incubated with 1.8 pmol full-length hnRNP K (lanes 1-4) and KH3 was added as competitor in 100, 200 and 400 fold molar excess (lanes 2-4). Lane 5 contains only the highest level of KH3 as control. 40 fmol [$^{32}$P]-labeled TAK1 mRNA 3'UTR fragment 3 (lanes 6 and 7) was incubated with 7.2 pmol full-length hnRNP K (lanes 6 and 7) and KH3 was added as competitor in 74 fold molar excess (lane 7).

FIG. 14: Reduction of hnRNP K results in enhanced TAK1 expression in untreated RAW 264.7 cells.

A) Western blot analysis of RAW 264.7 cells, which were transfected with no siRNA (lane 1), a control siRNA (ctrl.) (lane 2) or two siRNAs directed against hnRNP K (lanes 3 and 4). Antibodies detecting hnRNP K, TAK1 and Vinculin were applied.

B) Quantification of TAK1 normalized to Vinculin of the Western blot shown in A.

C) qRT-PCR analysis of the mRNAs isolated from two independent transfection experiments designed as in (A) with specific primers against TAK1 mRNA. Specific target mRNA was normalized to Ndufv1 mRNA and expressed as -fold change compared to mock transfected cells, set to 1.

Figure 15:
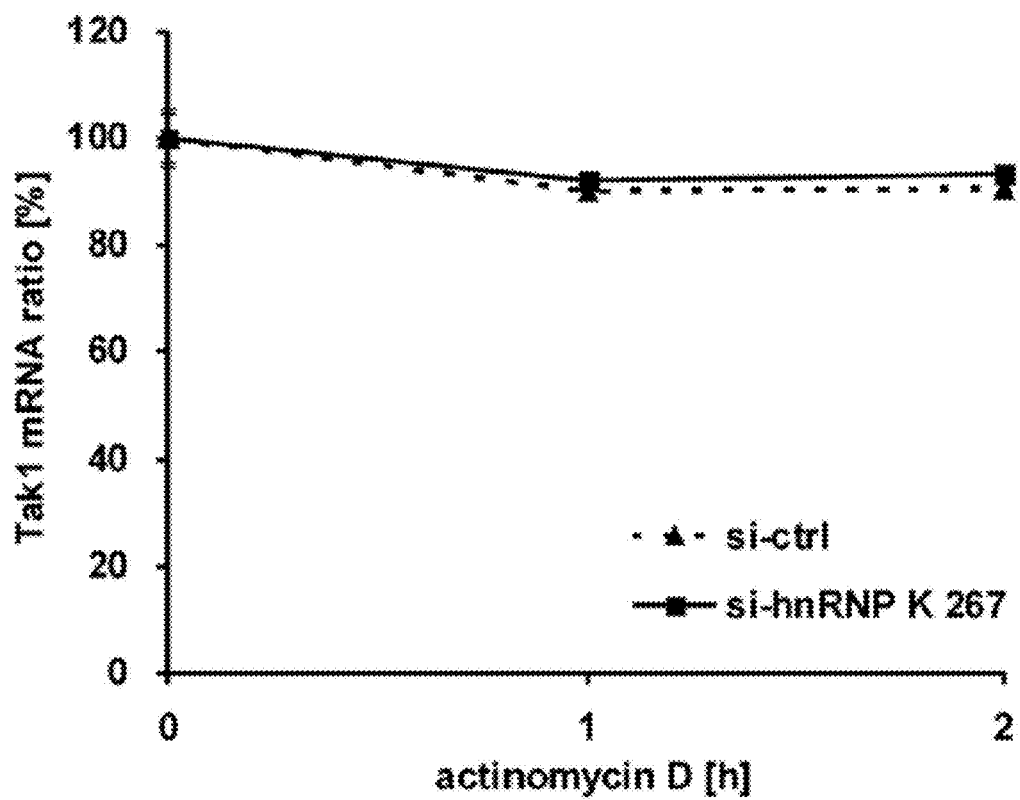

FIG. 15: Reduction of hnRNP K does not affect TAK1 mRNA stability in untreated RAW 264.7 cells.

Analysis of TAK1 mRNA stability by qRT-PCR. Cells were transfected with control siRNA (si-ctrl., triangles, dashed line) or hnRNP K siRNA (267, squares, solid line), treated with actinomycin D for 0, 1 and 2 h. TAK1 mRNA was normalized to Ndufv1 and GAPDH mRNAs (0 h time point 100%).

Figure 16:
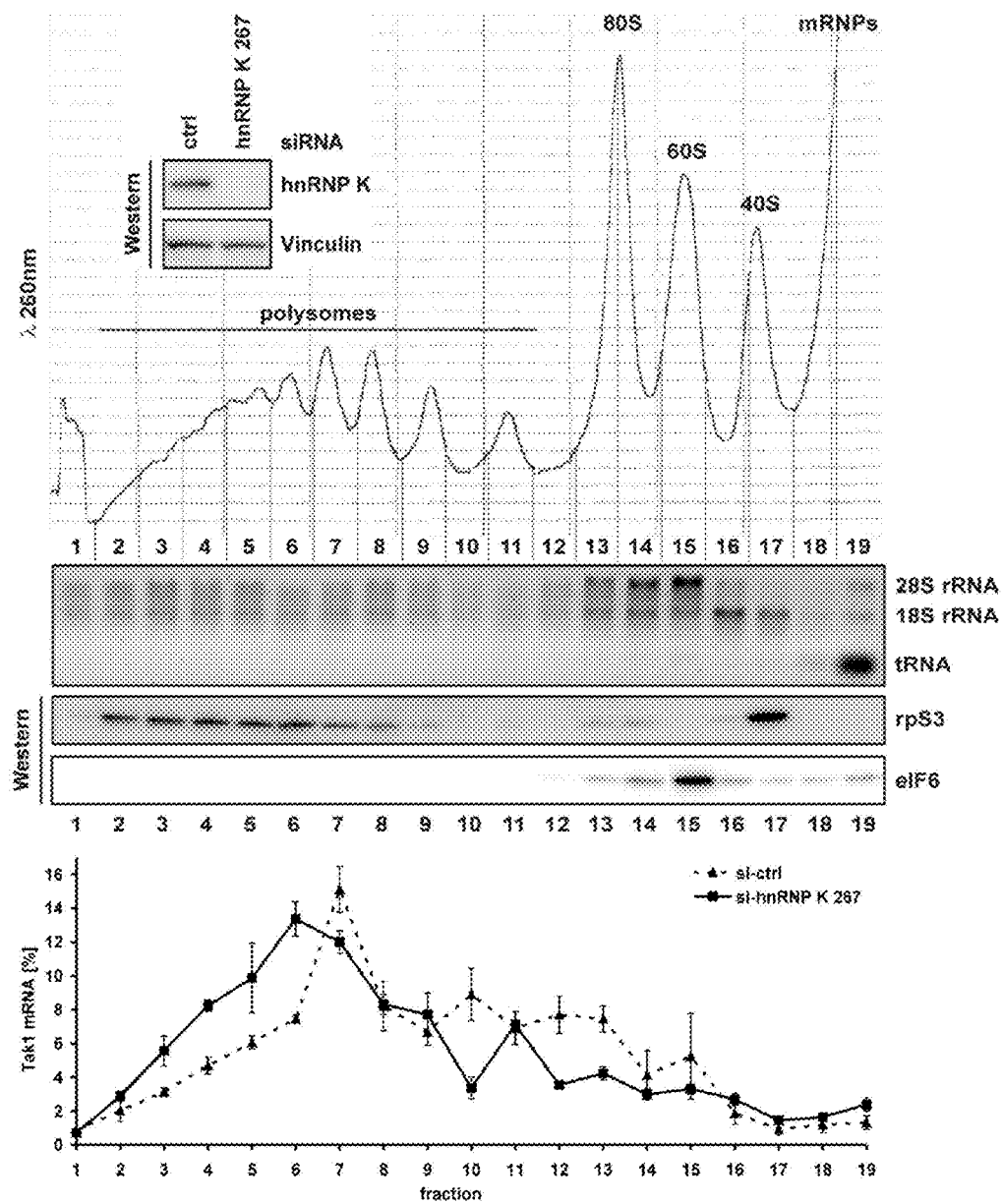

FIG. 16: Reduction of hnRNP K enhances TAK1 mRNA translation in untreated RAW 264.7 cells.

Top panel: Western blot analysis of cytoplasmic extracts generated from untreated RAW 264.7 cells, which were transfected with a control siRNA (ctrl.) or hnRNP K siRNA (267) with antibodies specific for hnRNP K and Vinculin.

Middle panel: A representative $A_{260\ nm}$ profile of cytoplasmic extracts characterized in the upper panel fractionated on 15-45% sucrose density gradients is shown. Polysomes, 80S ribosomes, 60S and 40S ribosomal subunits and mRNPs are indicated. RNA extracted from the 19 gradient fractions was visualized by gelred staining of an agarose gel. 18S and 28S rRNA are indicated. The distribution of rpS3 and eIF6 in the sucrose gradient fractions was determined by Western blotting.

Bottom panel: Endogenous TAK1 mRNA distribution in cytoplasmic extract generated from cells transfected with ctrl. (triangles, dashed line) or hnRNP K (267) siRNA (squares, solid line) was determined by qRT-PCR using the ΔCt-method and normalized to exogenously added LUC mRNA extraction control. The percentage of TAK1 mRNA in each fraction is shown.

Figure 17:
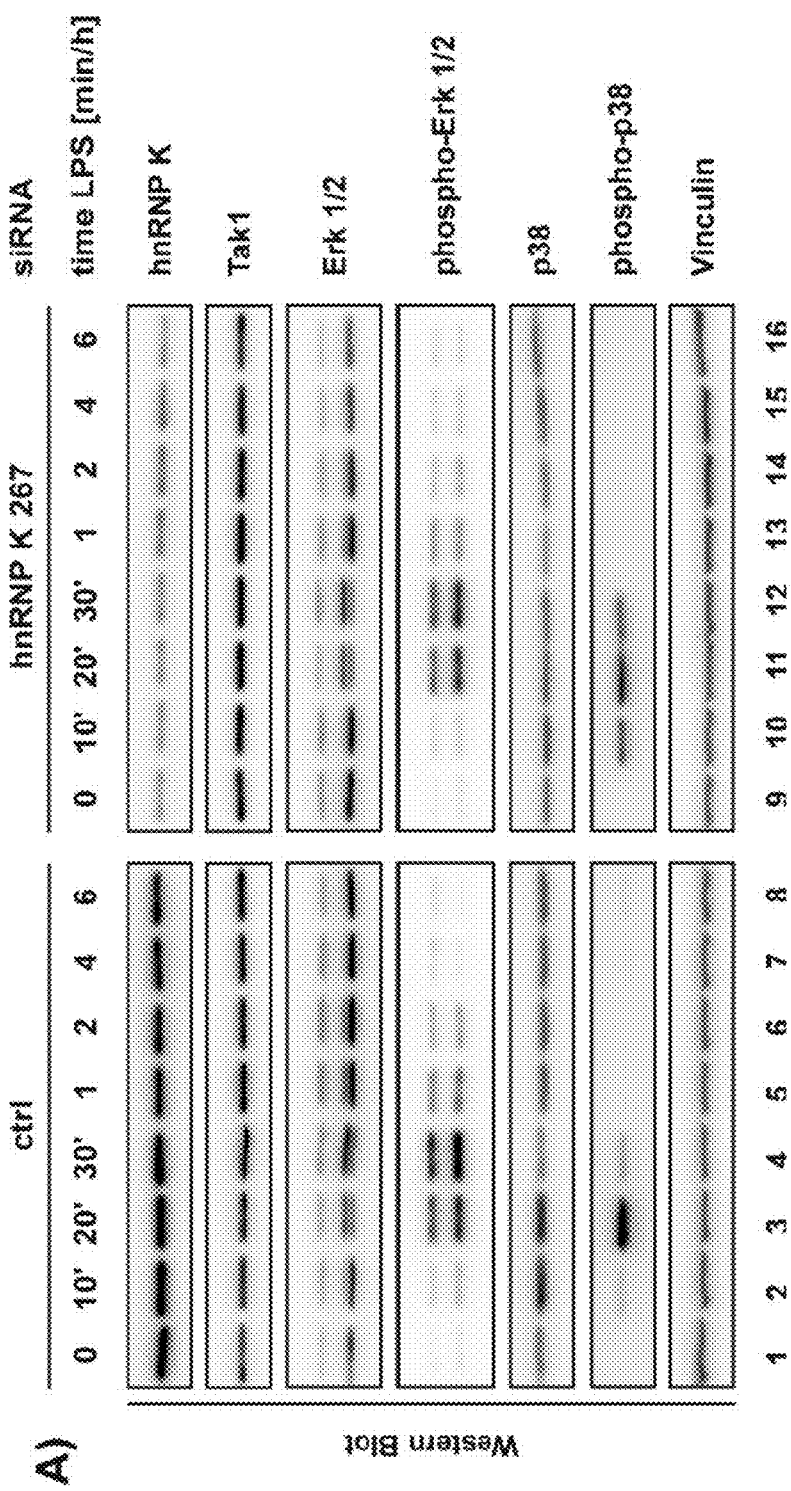
Figure 17:
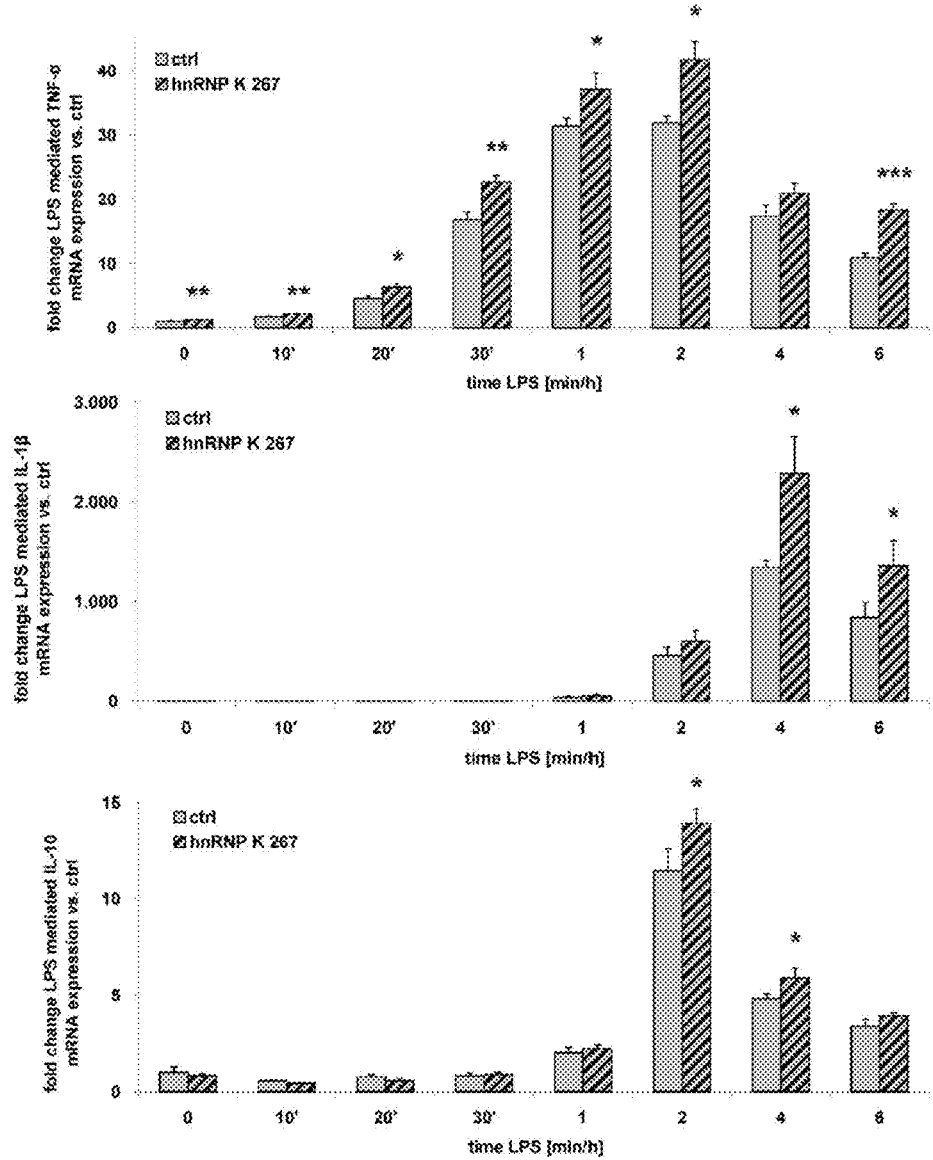

FIG. 17: LPS treatment of macrophages with reduced hnRNP K level that led to enhanced TAK1 protein expression shows an earlier and prolonged p38 phosphorylation and a stronger cytokine mRNA synthesis.

A) Western blot analysis of lysates generated from untreated RAW 264.7 cells, which were transfected with a control siRNA (ctrl.) (lanes 1-8) or hnRNP K siRNA (267) (lanes 9-16) with antibodies specific for hnRNP K, TAK1, ERK1/2, phospho-ERK1/2, p38, phospho-p38 and Vinculin.

B) Endogenous TNF-α, IL-1β and IL-10 mRNAs were determined by qRT-PCR using the ΔΔCt-method and normalized to Ndufv1 mRNA.

Figure 18:
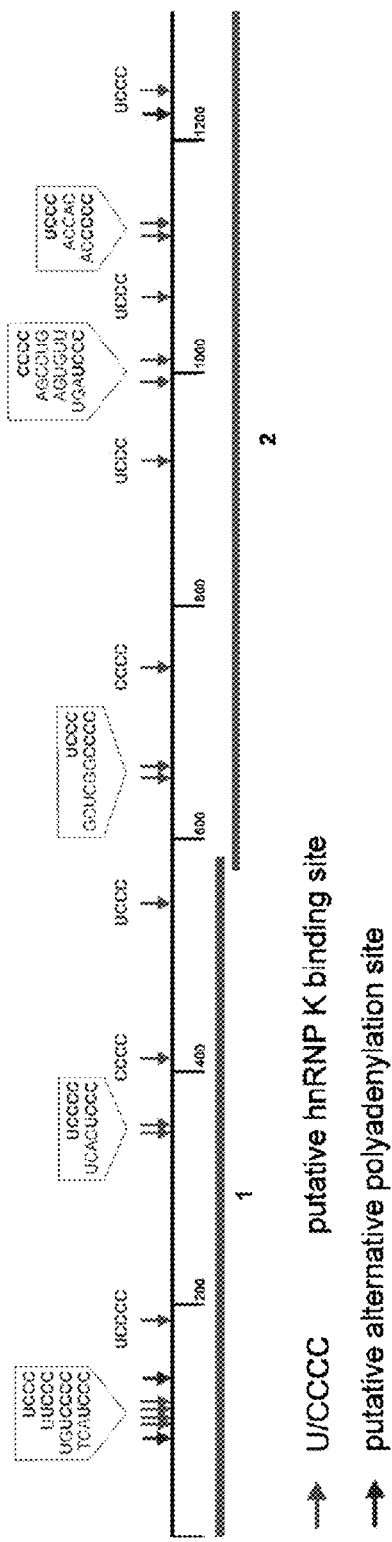

FIG. 18: Schematic representation of AKT2 mRNA 3'UTR.

Figure 19:
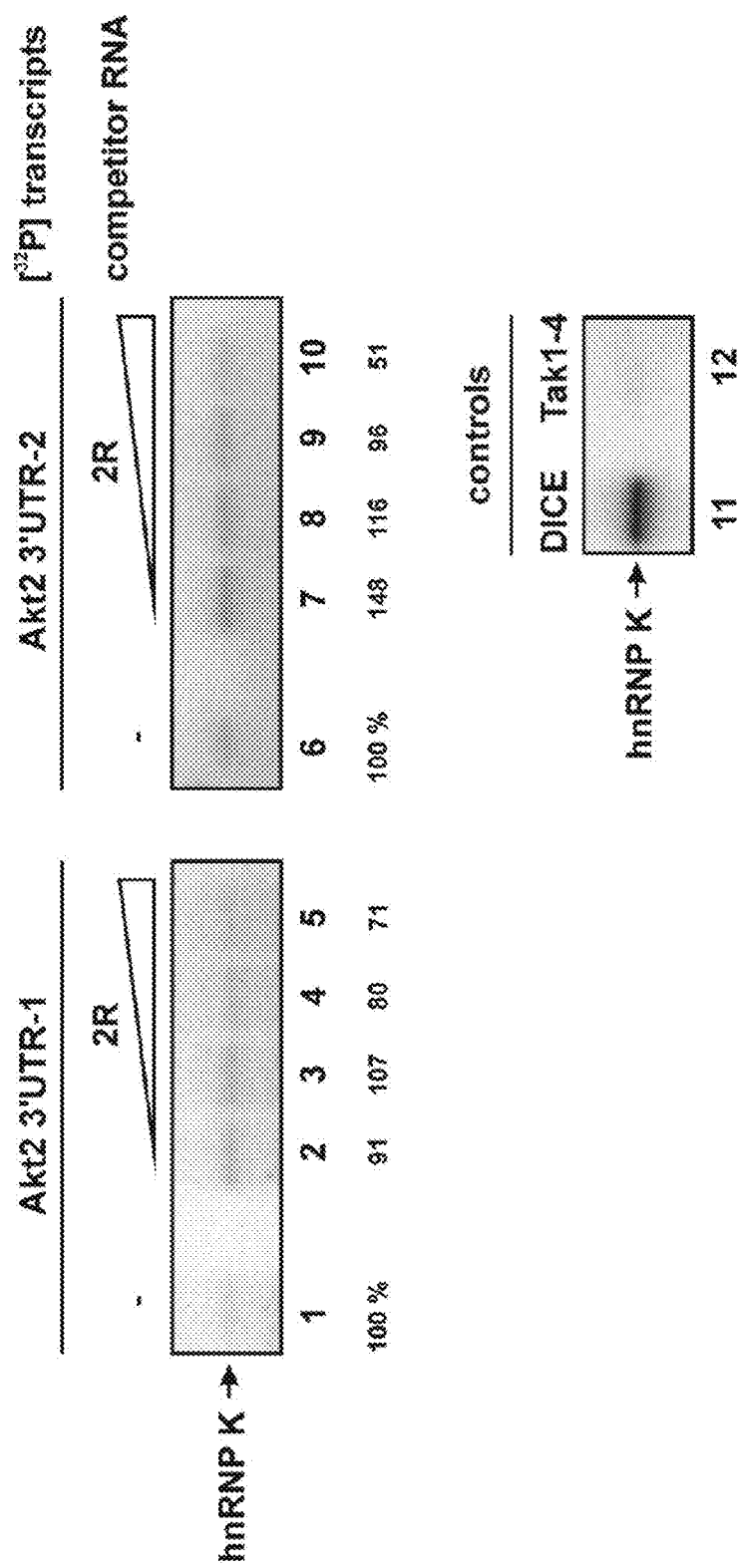

FIG. 19: 2R competes binding of hnRNP K to the Akt2 mRNA 3'UTR.

40 fmol [$^{32}$P]-labeled Akt2 mRNA fragment 1 (lanes 1-5), Akt2 mRNA 3'UTR fragment 2 (lanes 6-10), r15-LOX mRNA 3'UTR DICE (lane 11) or TAK1 mRNA 3'UTR fragment 4 (lane 12) was incubated with 7.2 pmol hnRNP K (lanes 1-12) in the presence of 10, 50, 100 or 200 fold molar excess of unlabeled competitor RNA 2R (lanes 2-5 and lanes 7-10).

Figure 20:
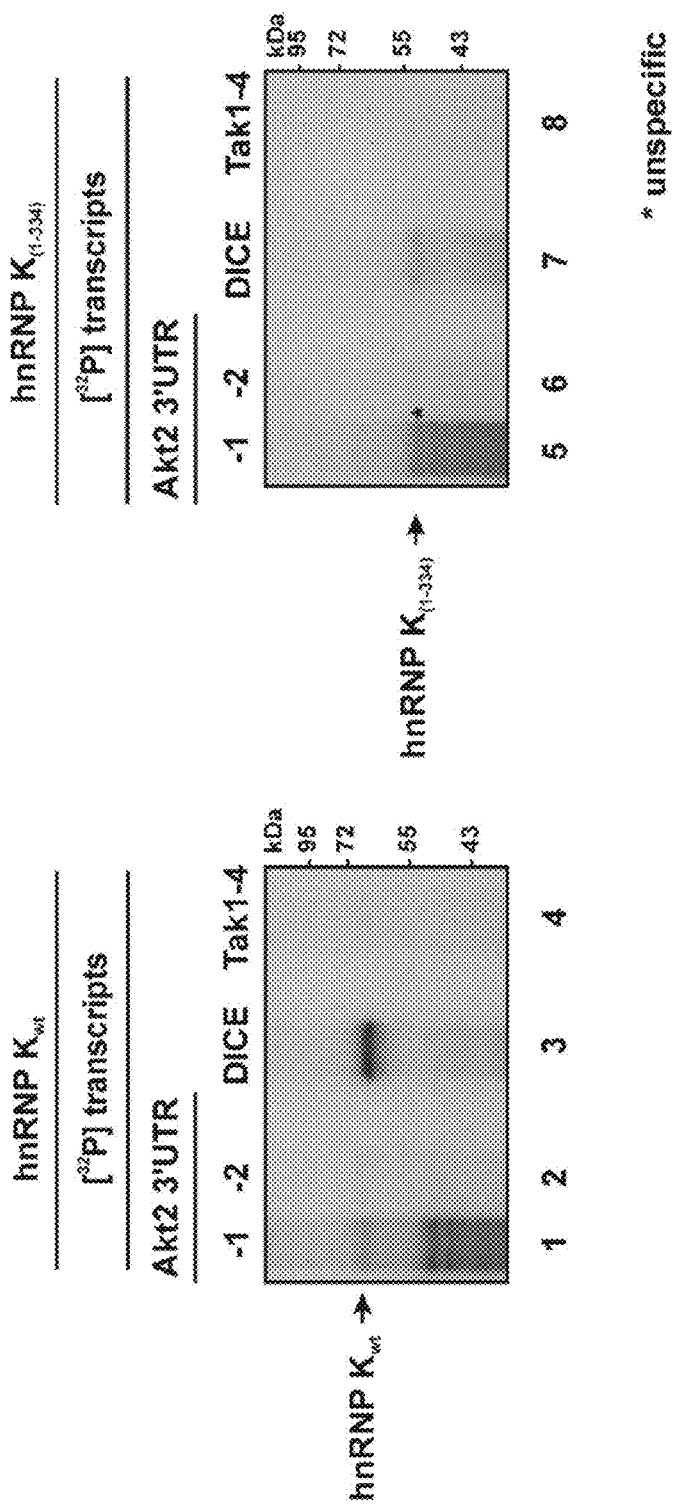

FIG. 20: HnRNP $K_{(1-334)}$ does not interact with the Akt2 mRNA 3'UTR.

40 fmol [$^{32}$P]-labeled fragments of the Akt2 mRNA 3'UTR as indicated (lanes 1, 2 and lanes 5, 6), the DICE of the r15-LOX mRNA (lanes 3 and 7) or TAK1 mRNA 3'UTR fragment 4 (lanes 4 and 8) was incubated with 3.6 pmol recombinant hnRNP $K_{wt}$ (lanes 1-4) or hnRNP $K_{(1-334)}$ (lanes 5-8). (*) marks an unspecific band.

Figure 21:
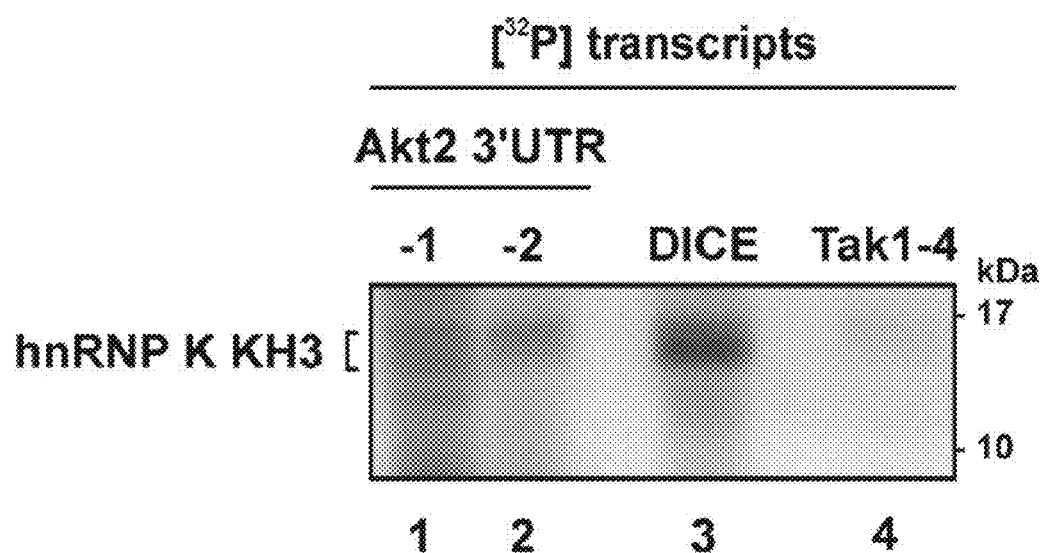

FIG. 21: KH3 of hnRNP K interacts with the Akt2 mRNA 3'UTR.

40 fmol [$^{32}$P]-labeled fragments of the Akt2 mRNA 3'UTR as indicated (lanes 1 and 2), the DICE of the r15-LOX mRNA (lane 3) and the TAK1 mRNA 3'UTR fragment 4 (lane 4) were incubated with 530 pmol recombinant KH3.

FIG. 22: Reduction of hnRNP K does not influence Akt2 mRNA level or mRNA stability.

A) Western blot analysis of untreated RAW 264.7 cells (lanes 1-4) or after 6 h LPS treatment (lanes 5-8), which were transfected with no siRNA (lanes 1 and 5), a control siRNA (ctrl.) (lanes 2 and 6) or two siRNAs directed against hnRNP K (lanes 3, 4, 7 and 8) with antibodies against hnRNP K and Vinculin.

B) qRT-PCR analysis of the mRNAs isolated from the transfection experiments designed as in A) with specific primers against Akt2 mRNA. Specific target mRNA was normalized to Ndufv1 mRNA and expressed as -fold change compared to mock transfected cells, set to 1.

C) Analysis of Akt2 mRNA stability by qRT-PCR. Cells were transfected with control siRNA (si-ctrl., triangles, 0h black dashed line, 6 h LPS grey dashed line) or hnRNP K siRNA (267, squares, 0 h black solid line, 6 h LPS grey solid line), treated with actinomycin D for 0, 1 and 2 h. Akt2 mRNA was normalized to Ndufv1 mRNA (0 h time point 100%).

Figure 23:
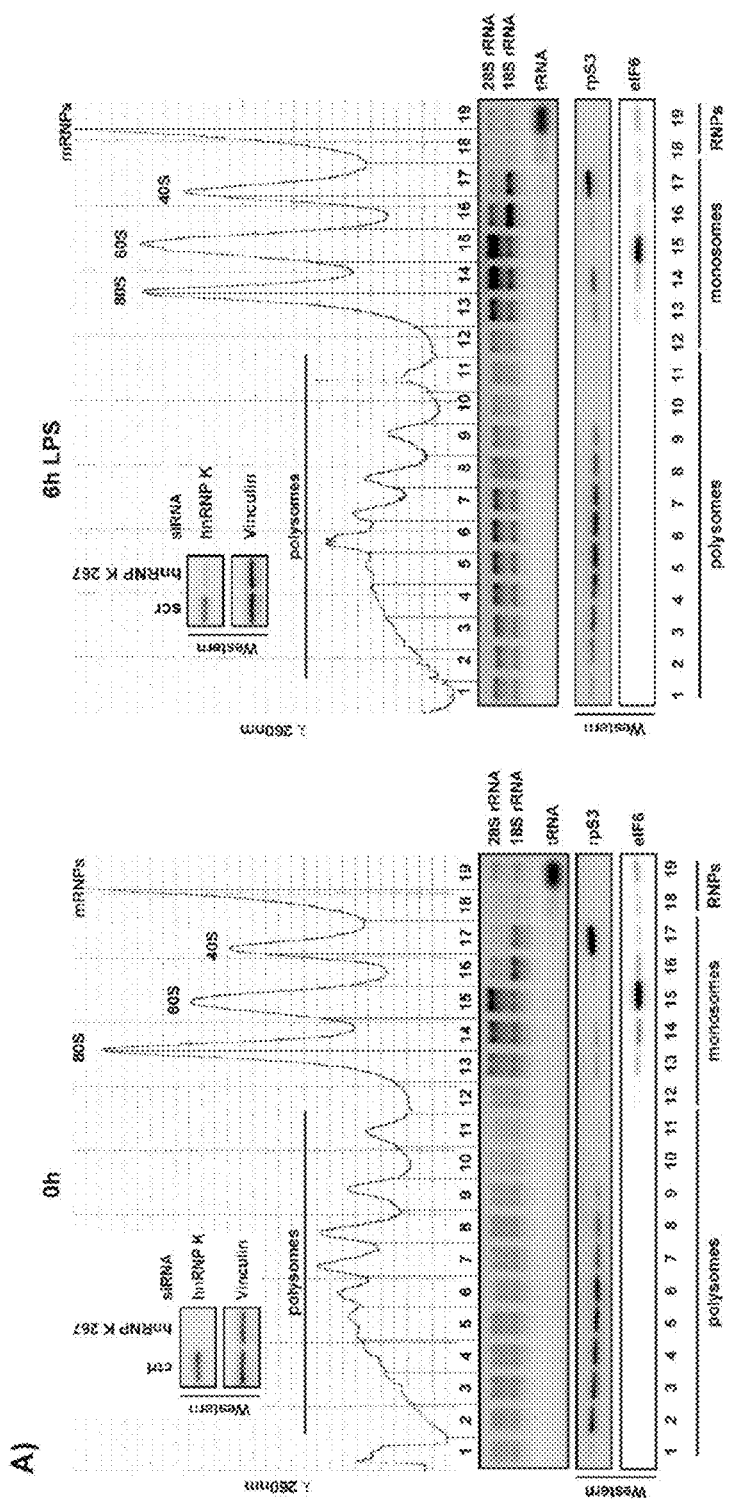
Figure 23:
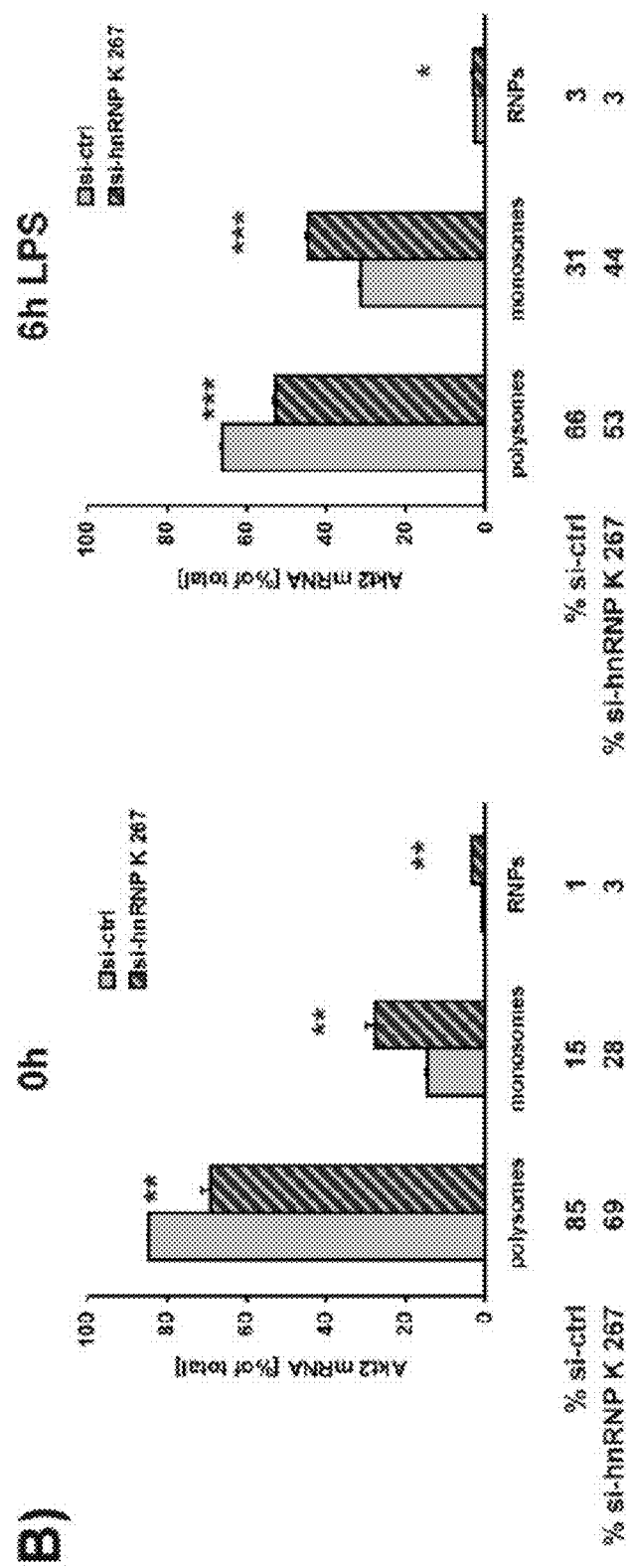
Figure 23:
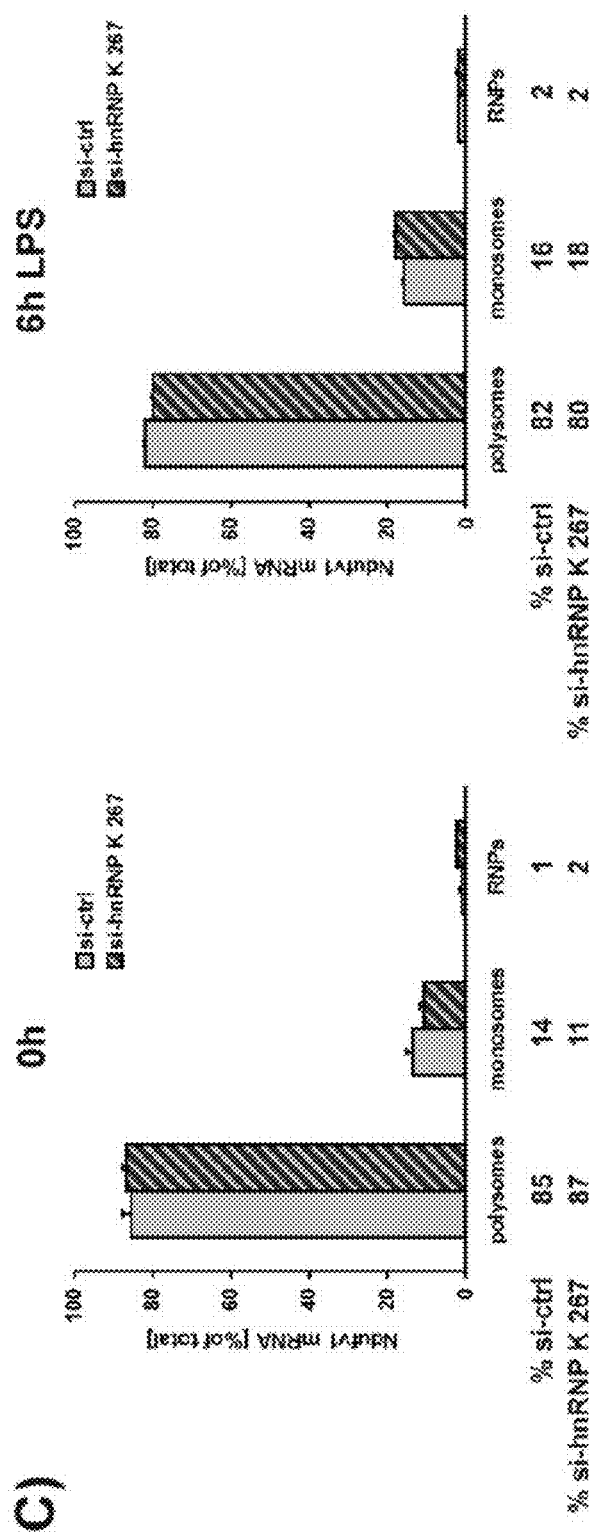

FIG. 23: Reduction of hnRNP K reduces Akt2 mRNA translation in untreated RAW 264.7 cells and after 6 h LPS.

A) Top panel: Western blot analysis of cytoplasmic extracts generated from untreated RAW 264.7 cells or after 6 h LPS treatment, which were transfected with a control siRNA (ctrl.) or hnRNP K siRNA (267) with antibodies specific for hnRNP K and Vinculin. Middle panel: Representative A260 nm profiles of cytoplasmic extracts characterized in the upper panel fractionated on 15-45% sucrose density gradients is shown. Polysomes, 80S ribosomes, 60S and 40S ribosomal subunits and mRNPs are indicated. RNA extracted from the 19 gradient fractions was visualized by gelred staining of an agarose gel. 18S and 28S rRNA are indicated. The distribution of rpS3 and eIF6 in the sucrose gradient fractions was determined by Western blotting.

B) Endogenous Akt2 mRNA distribution in pooled gradient fractions as indicated was determined by qRT-PCR using the ΔCt-method and normalized to exogenously added LUC mRNA extraction control. The percentage of Akt2 mRNA is shown.

C) Endogenous Ndufv1 mRNA distribution in pooled gradient fractions as indicated was determined by qRT-PCR using the ΔCt-method and normalized to exogenously added LUC mRNA extraction control. The percentage of Ndufv1 mRNA is shown.

Figure 24:
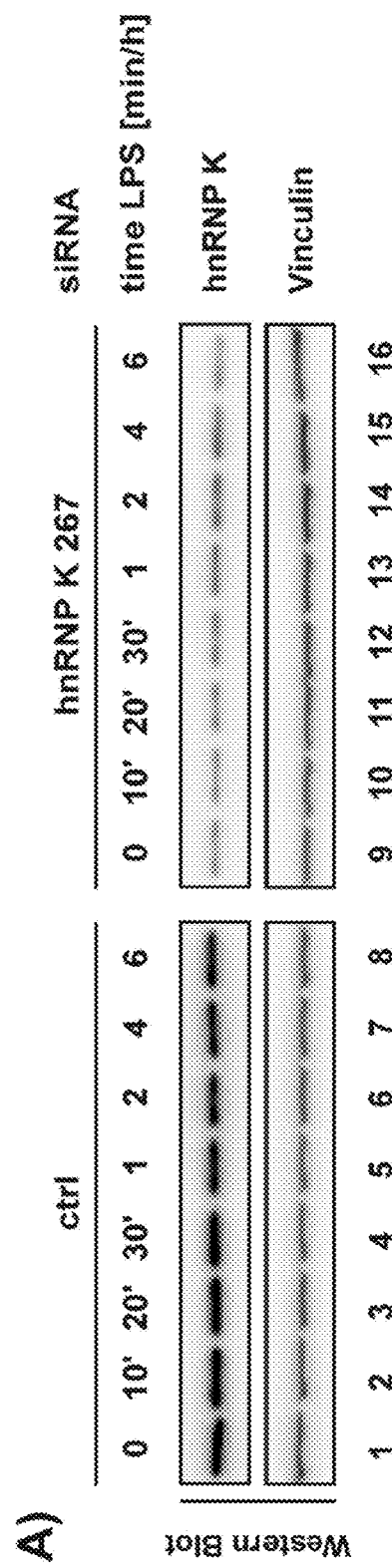
Figure 24:
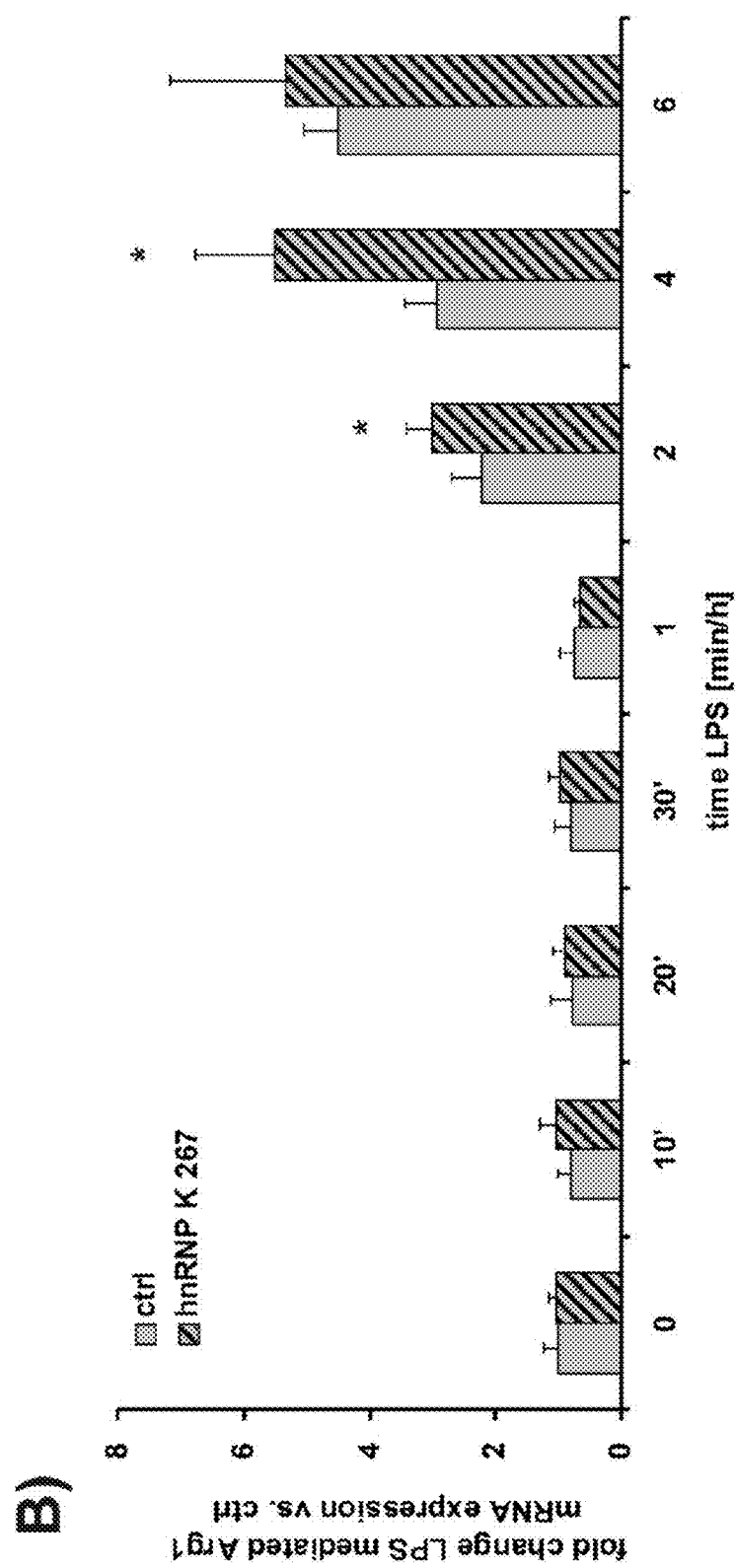

FIG. 24: LPS treatment of cells with reduced hnRNP K level that led to reduced Akt2 protein expression showed a stronger Arg1 mRNA synthesis.

A) Western blot analysis of lysates generated from untreated RAW 264.7 cells, which were transfected with a control siRNA (ctrl.) (lanes 1-8) or hnRNP K siRNA (267) (lanes 9-16) with antibodies specific for hnRNP K and Vinculin.

B) Endogenous Arg1 mRNA was determined by qRT-PCR using the ΔΔCt-method and normalized to Ndufv1 mRNA.

The present invention will now be further illustrated in the following examples without being limited thereto.

EXAMPLES

Example 1

To obtain insight into the impact of post-transcriptional control of gene expression on LPS induced TLR4 signaling, in particular the function of regulatory mRNA protein complexes, RAW 264.7 cell culture was employed, which allowed the generation of the number of cells that is necessary to produce extracts for biochemical experiments. Additionally, protocols were established to isolate and cultivate BMDM from healthy C57BL/6 mice as a tool to validate newly identified mRNAs and regulatory proteins involved in the post-transcriptional control of TLR4 signaling. It was decided to use C57BL/6 mice, because several relevant knock-out models were derived from this strain.

The required LPS concentration to induce RAW 264.7 cells (10 ng/ml) and BMDM (80 ng/ml) was determined in titration experiments. When RAW 264.7 cells were treated with LPS, the time dependent induction of ERK and p38 could be detected. Interestingly, BMDM from healthy C57BL/6 mice showed an earlier response than RAW 264.7 cells. Furthermore, a time dependent induction of mRNAs that encode pro-inflammatory cytokines (TNFα, IL-1β, IL-6, IL-15, IL-18), the anti-inflammatory cytokine IL 10 and COX-2 mRNA was observed, as monitored by RT-PCR. The expression of hnRNP K was not affected by LPS stimulation in both cell types, as confirmed by Western blotting. The caspase-3 cleavage product occurred only after 24 hrs, indicating that the cells did not undergo apoptosis at earlier time points (FIG. 2). For further analyses, time points 0, 20 min, 1, 2, 6 and 10 h were chosen.

To characterize activated macrophages, FACS analysis was performed. Living cells were analyzed for the expression of CD11b, CD115 and F4/80 (specific macrophage markers) with a FACSCanto II. Positive cells showed increased expression of activation markers (Gr1, MHCII, CD14, CD40, CD80 and CD86) compared to untreated cells (FIG. 3).

Further, cytoplasmic extracts were prepared from untreated RAW 264.7 cells and after LPS stimulation. Translation activity was monitored using Luciferase (Luc) reporter constructs bearing a 5'm7G-cap and a poly(A) tail. An increase in Luc activity in extracts prepared from cells treated with LPS for 6 h and 10 h compared to untreated cells was observed. Reporter mRNAs were extracted from translation reactions and mRNA stability was measured by qRT-PCR, showing that enhanced Luc activity was not a result of increased mRNA stability (FIG. 4).

To identify new translational regulated mRNAs by microarray analysis, it was focused on hnRNP K as a regulatory RNA binding protein. hnRNP K was immunoprecipitated with an anti-hnRNP K antibody from cytoplasmic extracts (CXT) of untreated RAW 264.7 cells and BMDM or from cells stimulated with LPS for 6 h, but not with a nonrelated control antibody (FIG. 5, upper panel). Endogenous c-Src mRNA coprecipitated with hnRNP K, as shown before in K562 cells. Interestingly, c-Src mRNA is not present in untreated RAW 264.7 cells and BMDM, but its synthesis is induced by LPS. Previously in THP-1 cells, it has been shown that hnRNP K interacts with the COX-2 mRNA that was used as a second positive control. Myosin X served as negative control.

Example 2

After immunoprecipitation, mRNAs were purified, converted to cDNAs and analyzed on an Affymetrix Mouse Genome 430 2.0 and 3'IVT array. By comparing input, anti-hnRNP K and control immunoprecipitation of untreated RAW 264.7 cells or after 6 h LPS stimulation, each in duplicates, 1901 differentially regulated mRNAs were found. Interestingly, 177 mRNAs were identified that encode proteins involved in immune response.

To further validate the list of newly identified hnRNP K-associated mRNAs, 21 candidate mRNAs (Tab. 1) were initially selected that encode factors acting mostly in the TLR4 signaling and associated downstream pathways and their expression was analyzed by qRT-PCR.

TABLE 1

Identified target mRNAs that were specifically enriched in hnRNP K immunoprecipitation.

| # | Gene Symbol | Gene Title | Gene ID |
|---|---|---|---|
| 1 | Pcgf1, Nspc1, AU024121 | polycomb group ring finger 1 | 69837 |
| 2 | Pcgf2, Mel18, Rnf110, Zfp144 | polycomb group ring finger 2 | 22658 |
| 3 | Med9, Med25 | mediator of RNA Polymerase II transcription, subunit 9 homolog (yeast) | 192191 |
| 4 | Irak1, IRAK, Plpk, mPLK, Il1rak | interleukin-1 receptor-associated kinase 1 | 16179 |
| 5 | Carm1, Prmt4 | coactivator-associated arginine methyltransferase 1 | 59035 |
| 6 | Litaf, TBX1, N4WBP3 | LPS-induced TN factor | 56722 |
| 7 | Icam2, CD102, Ly-60 | intercellular adhesion molecule 2 | 15896 |
| 8 | Fcer1g, Fce1g, Ly-50 | Fc receptor, IgE, high affinity I, gamma polypeptide | 14127 |
| 9 | Alox5, 5LO, 5LX, 5-LOX | arachidonate 5-lipoxygenase | 11689 |
| 10 | CD115, Csf1r, Fms, Csfmr, Fim-2, M-CSFR | colony stimulating factor 1 receptor | 12978 |
| 11 | Pik3ca, p110, caPI3K, p110alpha | phosphatidylinositol 3-kinase, catalytic, alpha polypeptide | 18706 |
| 12 | Irak1bp1, Aabp3, Aip70, Simpl | interleukin-1 receptor-associated kinase 1 binding protein 1 | 65099 |

TABLE 1-continued

Identified target mRNAs that were specifically
enriched in hnRNP K immunoprecipitation.

| #  | Gene Symbol | Gene Title | Gene ID |
|----|-------------|------------|---------|
| 13 | Irak4, NY-REN-64 | interleukin-1 receptor-associated kinase 4 | 266632 |
| 14 | Tak1, Map3k7 | mitogen-activated protein kinase kinase kinase 7 | 26409 |
| 15 | Nkrf | NF-kappaB repressing factor | 77286 |
| 16 | Erc1, ELKS, Rab6ip2 | ELKS/RAB6-interacting/CAST family member 1 | 111173 |
| 17 | Jun, AP-1, Junc, c-jun | Jun oncogene | 16476 |
| 18 | Akt1, Akt, PKB, Rac, PKB/Akt, PKBalpha | thymoma viral proto-oncogene 1 | 11651 |
| 19 | Akt2, PKB, PKBbeta, Akt2 | thymoma viral proto-oncogene 2 | 11652 |
| 20 | Akt3 | hymoma viral proto-oncogene 3 | 23797 |
| 21 | IRF7 | interferon regulatory factor 7 | 54123 |

Example 3

As a first criterion of exclusion, it was tested whether the selected 21 mRNAs show an equal expression in untreated RAW 264.7 cells and after 6 h LPS stimulation, indicating that transcriptional control of these mRNAs on the one hand and regulation of mRNA translation on the other can be distinguished. For 13 mRNAs, an equal amplification could be detected from the RNA pool isolated from control and LPS-treated RAW 264.7 cells, which was used for hnRNP K immunoprecipitation (data not shown).

Next, it was investigated whether the 13 equally expressed mRNAs show a specific enrichment with hnRNP K in untreated cells, but not LPS stimulated cells. Five mRNAs, for which no interaction with hnRNP K could be detected in the microarray analysis, served as negative controls (data not shown). For seven mRNAs with equal expression levels, a stronger enrichment on hnRNP K was determined in untreated RAW 264.7 cells compared to 6 h LPS stimulation. In contrast, the other five mRNAs were bound stronger by hnRNP K after LPS stimulation, while one mRNA was equally bound (FIG. 6).

Among the first group of seven, mRNAs that encode IRAK4, TAK1, IRAK1BP1, Erc1, CARM1/PRMT4, PIK3ca and Akt3 were identified. The kinases IRAK4 and TAK1 play essential roles in the MyD88 dependent TLR4 signaling pathway. IRAK1BP1 has an inhibitory function in inflammation. Erc1 is an IκB kinase regulatory subunit that is required for NFκB activation and CARM1/PRMT4 has been shown to function as a promoter-specific regulator of NFκB. LPS is implicated in the activation of the PI3K and Akt pathway in monocytes/macrophages. The PI3K family consists of three classes: IA, B, II and III. A dependence of LPS induced Akt activation on class IA PI3K has been shown by RNAi mediated PIK3ca silencing in monocytes.

Example 4

Next it was hypothesized that silencing of target mRNA translation by hnRNP K is abolished when the protein is released upon LPS stimulation. To address this issue, investigation was started as to whether LPS stimulation affects the differential distribution of target mRNAs to polysomes and translational inactive mRNPs through the use of sucrose gradient analysis of RAW 264.7 CXTs (FIG. 7).

Before harvesting, untreated or 6 h LPS stimulated RAW 264.7 cells were treated with cycloheximide, which inhibits the peptidyltransferase reaction and stalls translating ribosomes. CXTs prepared from these cells were fractionated on 15-45% sucrose gradients (FIG. 7A).

The distribution of 18S and 28S rRNA was used to analyze the position of ribosomal complexes and mRNPs (FIG. 7B, C). 28S and 18S rRNA accumulated in bottom fractions 2 to 8 (polysomes) and in fractions 13 and 14 (80S ribosomes), while fractions 16 and 17 contained mainly 18S rRNA of 40S ribosomal subunits (FIG. 7B, C). EIF6, a translation initiation factor that is bound to the ribosomal 60S subunit prior to 80S ribosome formation, was enriched in fraction 15. HnRNP K was mainly distributed to fractions 18 and 19, indicating that it is associated with mRNPs in untreated RAW 264.7 cells and after 6 h LPS stimulation (FIG. 7B, C). The enhanced distribution of ribosomal RNAs to polysomal fractions after 6 h of LPS treatment indicates an increase in mRNA translation (FIG. 7C).

Example 5

As a proof of principle, the distribution of the TNFα mRNA in the sucrose gradient profiles was analyzed next. Consistent with previous results, a shift of the TNFα mRNA from light polysomes to heavy polysomes was observed after 6 h LPS stimulation (FIG. 8).

Example 6

For two mRNAs that encode the critical kinases TAK1 and Akt2, which act in different branches of the TLR4 signaling pathway, the experimental strategy is summarized herein.

With the experiments outlined below it is shown that:
hnRNP K interacts directly with specific sequence elements in the 3' untranslated region (3'UTR) of TAK1 and Akt2 mRNA.
Binding of hnRNP K modulates TAK1 mRNA and Akt2 mRNA translation specifically in an LPS-dependent manner.
Translation control by hnRNP K results in enhanced TAK1 and reduced Akt2 synthesis, which is in agreement with their differential functions in TLR4 downstream signaling.
LPS-induced modulation of TAK1 and Akt2 mRNA translation by hnRNP K has a downstream impact on the pro- and anti-inflammatory cytokine expression.

Importantly, the hnRNP K mRNA interaction can be competed with:
a small peptide (79aa)
a small nucleic acid (38nts),
as shown in FIGS. 10, 13 and 19.

The analysis of mRNAs that are equally expressed in untreated and LPS-activated macrophages revealed that binding of hnRNP K to 13 mRNAs that encode mostly TLR4 downstream signaling proteins is significantly enhanced or decreased (FIG. 6). These mRNAs are potential targets of hnRNP K-mediated translational regulation and changes in the respective protein levels will affect TLR4 downstream-signaling, which results in modulated pro- and anti-inflammatory cytokine expression.

Two mRNAs were chosen to prove that the synthesis of TLR4 downstream signaling proteins is regulated by hnRNP K in an LPS-dependent manner and the resulting modulation of TLR4 signaling affects pro- and anti-inflammatory cytokine expression:

Tak1: Transforming growth factor-β (TGFβ) activated kinase 1 (TAK1) mRNA was stronger enriched on hnRNP K in untreated RAW 264.7 cells compared to 6 h LPS stimulation (cf. FIG. 6).

Akt2: In contrast, a stronger binding to hnRNP K was determined for Akt2 mRNA after LPS stimulation (cf. FIG. 6).

TAK1

TAK1, a MAP3K member, is the central kinase of the MyD88-dependent branch in TLR4 signaling (FIG. 1), which leads to the activation of IκB kinases (IKK) in the NFκB pathway (early response) and the three MAPK pathways: ERK 1/2, c-Jun N-terminal kinase (JNK) and p38. MyD88 recruits the kinases IRAK1 and IRAK4. IRAK1, a target of IRAK4 recruits tumor necrosis factor (TNF) receptor associated factor 6 (TRAF6) to the TLR4-receptor complex. The IRAK1-TRAF6 complex dissociates from the TLR4-receptor complex and activates TAK1. TAK1 phosphorylates MKK4, MKK3/6 and IKK, which activate JNK and p38 pathways and induce IκB degradation leading to NFκB activation. These signaling pathways upregulate transcription factors including NFκB and AP-1, implicated in the coordinated induction of pro-inflammatory (TNFα, IL-1β) and anti-inflammatory (IL-10) cytokine encoding genes.

TAK1 mRNA 3' untranslated region (UTR) was screened for the presence of potential hnRNP K binding sequence motifs. It contains several CU-rich (U/CCCC) elements, which were first identified as hnRNP K binding motifs in the differentiation control element (DICE) (241nts) of reticulocyte 15-Lipoxygenase (r15-LOX) mRNA 3'UTR. HnRNP K is a potent regulator of r15-LOX mRNA translation in erythroid cell maturation. DICE binding is conferred by the third hnRNP K homology domain (KH3) of hnRNP K. The TAK1 mRNA 3'UTR (>3600 nts) were divided into eight fragments (1.1, 1.2, 2, 3, 4, 5.1, 5.3 and 6) to analyze direct interaction with hnRNP K in in vitro UV-crosslinking assays with [$^{32}$P]-labeled transcripts (FIG. 9, lanes 1-8). Fragments 3, 5.1 and 5.3 were strongly bound by recombinant His-hnRNP K, the DICE served as positive control (FIG. 9, lanes 4, 6, 7 and 9). Interestingly, fragment 4 that contains a class I AU-rich element (ARE) did not interact (FIG. 9, lane 5).

Signals for fragment 5.1 and 5.3 were comparable and fragment 6 did not interact, suggesting that U/CCCC elements in fragment 5.1 mediate the interaction with hnRNP K. Next, it was investigated whether a short fragment of the DICE (2R) (38nts) that is sufficient to mediate r15-LOX mRNA translation regulation is able to compete hnRNP K binding to TAK1 mRNA fragments 3 and 5.1. 2R did compete the interaction of hnRNP K with fragments 3 and 5.1 (FIG. 10, lanes 2-5 and 7-10), further indicating that hnRNP K binds to the CU-rich sequence.

Previously, it has been shown that DICE-binding of hnRNP K lacking KH3 (hnRNP K$_{(1-334)}$) was significantly reduced. To prove that deletion of KH3 results in loss of interaction with TAK1 mRNA fragments 3 and 5.1, UV-crosslinking of [$^{32}$P]-labeled fragments 3 and 5.1 with full length His-hnRNP K and truncated His-hnRNP K$_{(1-334)}$ was performed. Fragment 4 served as negative and the DICE as positive control (FIG. 11). HishnRNP K was specifically bound to fragment 3 and 5.1 and the DICE, but not fragment 4 (FIG. 11, lanes 1-4). In contrast, binding of His-hnRNP K$_{(1-334)}$ to fragment 3, 5.1 and the DICE RNA was strongly reduced (FIG. 11, lanes 5-8). Residual binding to the DICE results from non-specific interaction of KH1 and KH2 in the absence of KH3.

In order to prove that KH3 directly interacts with TAK1 mRNA fragments 3 and 5.1, His-KH3 was employed. Again, the DICE served as positive, fragment 4 as negative control (FIG. 12). His-KH3 specifically binds to fragment 3 and 5.1 and the DICE, but not fragment 4 (FIG. 12, lanes 1-4).

Next, it was investigated whether KH3 (79 amino acids) could function as a small peptide competitor that interferes with binding of full-length hnRNP K (463 amino acids). For this purpose the DICE or fragment 3 was exposed to full-length hnRNP K and recombinant KH3 in the same reaction (FIG. 13). KH3 competes for binding of full-length hnRNP K to the DICE or TAK1 mRNA 3'UTR fragment 3 (FIG. 13, lanes 1-7).

Having shown that recombinant hnRNP K directly interacts with the TAK1 mRNA 3'UTR, it was next investigated whether hnRNP K acts as a cellular regulator of TAK1 mRNA translation in murine macrophages (RAW 264.7). For this purpose, RNAi with two individual siRNAs that target hnRNP K (267, 1467) was performed. As a control, a nonrelated siRNA (ctrl.) was used (FIG. 14). Transfection of non-treated RAW 264.7 cells with the specific siRNAs strongly enhanced the expression of TAK1 protein (FIGS. 14 A and B).

To address the mechanism underlying enhanced TAK1 protein expression at reduced endogenous hnRNP K levels, it was first examined whether hnRNP K depletion resulted in an increase of TAK1 mRNA (FIG. 14C). TAK1 mRNA levels were not affected, indicating that enhanced transcription of the TAK1 gene did not account for elevated TAK1 protein synthesis (FIGS. 14 A and B). The stability of TAK1 mRNA could also be affected by hnRNP K.

To assess TAK1 mRNA stability after siRNA-mediated hnRNP K reduction, transcription was blocked by actinomycin D treatment. TAK1 mRNA stability remained unchanged when hnRNP K siRNA (267) or a control (ctrl.) siRNA were applied (FIG. 15). Taken together, these observations suggest that the increase in TAK1 protein is a consequence of enhanced Tak1 mRNA translation when hnRNP K is reduced.

To prove that endogenous TAK1 mRNA translation is up-regulated in cells transfected with the hnRNP K siRNA (267), TAK1 mRNA co-sedimentation with polysomes was characterized by fractionation of cytoplasmic extracts on 15 to 45% sucrose gradients (FIG. 16, bottom panel). MRNA translation was stalled by cycloheximide treatment before RAW 264.7 cells were harvested for extract preparation. The efficiency of the hnRNP K knock down in RAW 264.7 cells was analyzed by Western blotting (FIG. 16, top panel).

The distribution of 18S and 28S rRNA and Western blot analysis of rpS3, a ribosomal protein of the 40S ribosomal subunit and translation initiation factor eIF6 that is bound to the ribosomal 60S subunit prior to 80S ribosome formation were used to analyze the position of ribosomal complexes and mRNPs (FIG. 16, middle panel). 28S and 18S rRNA accumulated in bottom fractions 2 to 8 (polysomes) and in fractions 13 and 14 (80S ribosomes), while fractions 16 and 17 contained mainly 18S rRNA of 40S ribosomal subunits. RpS3 accumulated in 40S and 80S and complex-containing fractions (FIG. 16, middle panel). EIF6 was enriched in fraction 15 that contains 60S ribosomal subunits (FIG. 16, middle panel). The analysis of endogenous TAK1 mRNA distribution by qRT-PCR illustrates that hnRNP K knock down resulted in a strong accumulation of TAK1 mRNA in polysomal fractions (FIG. 16, bottom panel), indicating an enhanced translation of TAK1 mRNA in vivo. The results clearly show that hnRNP K down regulation enhances endogenous TAK1 mRNA translation resulting in an increase of TAK1 protein.

To obtain insight in the function of the regulatory mRNA protein complex it was investigated whether the reduction of hnRNP K that leads to enhanced TAK1 protein expression results in increased phosphorylation of downstream MAP kinases (p38 or ERK1/2) and to elevated cytokine mRNA synthesis. For this purpose, RAW 264.7 cells, which were transfected with a nonrelated control siRNA (ctrl.) (FIG. 17 A, left panel) or with the specific siRNA against hnRNP K (267) (FIG. 17 A, right panel) were treated with 10 ng/ml LPS for the indicated time points. A time dependent induction of ERK and p38 phosphorylation in RAW 264.7 cells, which were transfected with a control siRNA (ctrl.) (FIG. 17 A, left panel) was observed. Interestingly, knock down of hnRNP K by the specific siRNA (267) led to an earlier and prolonged phosphorylation of p38, but did not affect phosphorylation of ERK1/2 (FIG. 17 A, compare left and right panel). Importantly, synthesis of TNF-α, IL-1β and IL-10 mRNAs increased after reduction of hnRNP K by RNAi (FIG. 17 B).

Taken together, the above results indicate that binding of hnRNP K to the TAK1 mRNA 3'UTR inhibits TAK1 mRNA translation in untreated RAW 264.7 cells. The reduction of endogenous hnRNP K leads to an increase in TAK1 mRNA translation. When cells in which TAK1 protein expression is enhanced are treated with LPS an earlier and prolonged phosphorylation of p38 and an increase of cytokine mRNA synthesis can be detected, suggesting that hnRNP K is an important modulator of TAK1 mRNA translation that affects TLR-4 downstream signaling and induction of cytokine mRNA expression.

Akt2

LPS induced TLR-4 signaling activates the phosphatidylinositol 3 kinase (PI3K)/Akt pathway. The first kinase recruited and activated after PI3K activation is 3-phosphoinositide-dependent kinase (PDK-1). PDK-1 interacts and phosphorylates members of the Akt family of serine/threonine protein kinases (Akt1, Akt2 and Akt3). Activation of Akt (also known as PKB) results in the phosphorylation of a number of substrates that have potential importance in LPS signaling, like glycogen synthase kinase (GSK-3), caspase 9, IκB kinases. The three Akt family members are closely related and highly conserved. Recently it has been shown that specific down regulation of Akt2 level impaired chemotaxis of both THP-1 and mouse peritoneal macrophages, suggesting that Akt2 is required for macrophage trafficking. Furthermore it was reported that Akt kinases differentially contribute to macrophage polarization, with Akt1 knockout giving rise to an M1 and Akt2 ablation resulting in an M2 phenotype.

As shown before for TAK1 mRNA, the 3'UTR of the Akt2 mRNA was screened for the presence of potential hnRNP K binding elements. It contains several U/CCCC motifs (FIG. 18).

To analyze whether recombinant hnRNP K directly interacts with the Akt2 mRNA 3'UTR, UV-crosslinking experiments were performed with the [$^{32}$P]-labeled Akt2 mRNA 3'UTR subdivided in two fragments (1 and 2) (FIG. 19, lanes 1-5 and 6-10). Recombinant hnRNP K was bound strongly to both fragments (FIG. 19, lanes 1 and 6) and to the DICE, but not to the TAK1 mRNA 3'UTR fragment 4 that served as negative control (FIG. 19, lanes 11 and 12). Furthermore, it was investigated whether the short RNA consisting of 2 repeats of the DICE (2R) can be used to compete the binding of hnRNP K to the Akt2 mRNA 3'UTR fragments 1 and 2. As shown in FIG. 19, the hnRNP K-Akt2 mRNA interaction could be competed by the short ribonucleic acid 2R (FIG. 19, lanes 2-5 and 7-10), indicating that hnRNP K binds to the CU-rich sequence.

KH3 of hnRNP K is required for specific RNA interaction and RNA binding of hnRNP K lacking KH3 (hnRNP $K_{(1-334)}$) is strongly reduced. To prove that the KH3 peptide also mediates the interaction with Akt2 mRNA 3'UTR fragments 1 and 2, in vitro RNA binding was employed. His-hnRNP Kwt and the deletion variant His-hnRNP $K_{(1-334)}$ were incubated with [$^{32}$P]-labeled Akt2 mRNA 3'UTR fragments 1 and 2. The DICE served as positive and TAK1 mRNA 3'UTR fragment 4 as negative control (FIG. 20). Whereas His-hnRNP $K_{wt}$ is bound to the Akt2 mRNA 3'UTR fragment 1, 2 and DICE RNA, but not to TAK1 mRNA 3'UTR fragment 4 (FIG. 20, lanes 1-4), binding of His-hnRNP $K_{(1-334)}$ to fragment 1, 2 and DICE RNA is strongly reduced (FIG. 20, lanes 5-8).

To prove that the peptide KH3 specifically and directly interacts with Akt2 mRNA fragment 1 and 2, His-KH3 was incubated with [$^{32}$P]-labeled Akt2 mRNA fragment 1 and 2. The DICE and TAK1 mRNA 3'UTR fragment 4 were employed as positive and negative controls, respectively (FIG. 21, lanes 1-4). The peptide KH3 specifically interacts with Akt2 mRNA fragment 1 and 2 and DICE RNA, but not the TAK1 mRNA fragment (FIG. 21, lanes 1-4).

Having shown that recombinant hnRNP K directly interacts with the Akt2 mRNA 3'UTR, it was next investigated whether endogenous hnRNP K acts as a cellular regulator of Akt2 mRNA translation in murine RAW 264.7 macrophages in an LPS dependent manner. For this purpose, RNAi with two siRNAs that target hnRNP K (267, 1467), and a nonrelated control siRNA (ctrl.) were performed. The efficiency of the hnRNP K knock down was analyzed by Western blotting (FIG. 22A).

Next, it was examined whether hnRNP K depletion resulted in a reduced Akt2 mRNA level or decreased Akt2 mRNA stability. Akt2 mRNA levels and stability remained unchanged after hnRNP K knock down (FIGS. 22 B and C). To determine whether polysomal loading of Akt2 mRNA is affected by hnRNP K, Akt2 mRNA co-sedimentation was characterized with polysomes, monosomes or mRNPs in sucrose gradient analysis (FIG. 23).

RAW 264.7 cells, transfected with a nonrelated control siRNA (ctrl) or hnRNP K siRNA (267) were left untreated or treated for 6 h with LPS. MRNA translation was stalled by cycloheximide treatment before the cells were harvested. Cytoplasmic extracts were fractionated on 15 to 45% sucrose gradients. The efficiency of the hnRNP K knock down in RAW 264.7 cells is shown in the Western blot inserts (FIG. 23 A, upper panel). Fractions that contain polysomes (1-12), monosomes (12-17) and mRNPs (18-19) were pooled (FIG. 23 A, lower panel) to analyze endogenous Akt2 mRNA distribution. QRT-PCR analysis illustrates that hnRNP K knock down resulted in a strong accumulation of Akt2 mRNA in fractions containing monosomes and mRNPs (FIG. 23 B), indicating a decreased translation of Akt2 mRNA in untreated RAW 264.7 cells (left panel) that is further enhanced after 6 h LPS treatment (right panel). In contrast, translation of Ndufv1 mRNA remained unchanged (FIG. 23 C). These studies indicate that siRNA-mediated down regulation of endogenous hnRNP K results in an inhibition of endogenous Akt2 mRNA translation. Akt2 could not be detected immunologically, because a suitable antibody was not available.

To determine macrophage-specific functional consequences of hnRNP K mediated Akt2 regulation it was investigated whether reduced Akt2 mRNA translation caused by hnRNP K down regulation results in an M2 macrophage phenotype. M2 macrophage polarization and expression of arginase 1 (Arg1) are primarily regulated by the transcription factors C/EBPβ and STAT5. C/EBPβ levels are elevated in Akt2$^{-/-}$ macrophages or RAW 264.7 cells in which Akt2 expression is silenced compared with wildtype or Akt1-deficient cells. Increased C/EBPβ binding to the Arg1 promoter leads to an induction of Arg1 mRNA synthesis in Akt2$^{-/-}$ macrophages. RAW 264.7 cells, which were transfected with a nonrelated control siRNA (ctrl.) (FIG. 24 A, left panel) or with the specific siRNAs against hnRNP K (267) (FIG. 24 A, right panel) were treated with 10 ng/ml LPS for the indicated time points.

We could observe a time dependent induction of Arg1 mRNA synthesis in the control cells, which is significantly elevated in hnRNP K knock down cells (FIG. 24 B). Taken together, these results indicate that hnRNP K is an important modulator of Akt2 mRNA translation.

Discussion:

Pathogen components, such as bacterial LPS, that act through TLR4 lead to the activation of MAPKs and NFκB through different pathway branches to subsequently induce pro- and anti-inflammatory cytokine expression. The expression of kinases and their modulators involved in these processes is controlled both transcriptionally and post-transcriptionally. Post-transcriptional regulation of gene expression is mediated by trans-acting factors, like RNA-binding proteins at the level of mRNA stability and mRNA translation. This facilitates rapid responses to environmental changes.

To obtain insight into the function of regulatory mRNA-protein complexes RAW 264.7 cells and bone marrow derived macrophages (BMDM) from C57BL/6 mice were used. Macrophage maturation after LPS stimulation was confirmed by flow cytometry (FACS) and cytokine mRNA levels by RT-PCR.

To identify mRNAs, which are translationally regulated in an LPS dependent manner, cytoplasmic extracts (CXT) from untreated RAW 264.7 cells and BMDM and after 6 h LPS stimulation were generated. From these extracts a known modulator of mRNA translation, heterogeneous nuclear ribonucleoprotein (hnRNP) K was immunoprecipitated with a specific antibody. Coimmunoprecipitated mRNAs were applied to microarray analysis (Affymetrix Mouse Genome 430 2.0 and 3'IVT array). 1901 mRNAs were identified, which are differentially enriched on hnRNP K upon LPS treatment. Interestingly, 177 mRNAs encode proteins involved in the immune response. Initially, 21 candidate mRNAs were selected that encode mostly factors acting in the TLR4 pathway and their expression was analyzed by qRT-PCR. 13 mRNAs were equally amplified from the RNA pool isolated from control and LPS-treated RAW 264.7 cells, suggesting that these are regulated post-transcriptionally. A stronger specific enrichment on hnRNP K was determined in untreated RAW 264.7 cells compared to LPS stimulation for seven of these mRNAs, whereas five mRNAs were bound stronger by hnRNP K after LPS treatment. The first group of identified candidate target mRNAs encode IL-1R associated kinase-4 (IRAK4), transforming growth factor-β (TGFβ) activated kinase 1 (TAK1), IRAK1-binding protein 1 (IRAK1BP1), IκB kinase regulatory subunit (Erc1/ELKS), coactivator-associated arginine methyltransferase 1 (CARM1/PRMT4), phosphatidylinositol 3 kinase (PI3K) catalytic subunit p110a (PIK3ca) and thymoma viral protooncogene 3 (Akt3). It is therefore apparent that hnRNP K silences target mRNA translation in untreated macrophages, while the protein is released from the mRNA upon LPS stimulation. Earlier it has been shown that hnRNP K is a specific activator and substrate of the tyrosine kinase c-Src. c-Src-dependent phosphorylation of Y458 in hnRNP K leads to loss of specific mRNA binding and abolishes its function as an inhibitor of mRNA translation.

The invention claimed is:

1. A method of using a RNA oligonucleotide 2R, consisting of the nucleotide sequence shown in SEQ ID No: 2, for modulating a toll-like receptor 4 (TLR4) signaling pathway, wherein said RNA oligonucleotide down-regulates binding of heterogeneous nuclear ribonucleoprotein K (hnRNP K) to TAK1 mRNA by competition.

2. A method of administering a pharmaceutical composition, comprising a RNA oligonucleotide 2R, consisting of the nucleotide sequence shown in SEQ ID No: 2, for modulating a toll-like receptor 4 (TLR4) signaling pathway, wherein said RNA oligonucleotide down-regulates binding of heterogeneous nuclear ribonucleoprotein K (hnRNP K) to TAK1 mRNA by competition.

3. The method according to claim 2, wherein the pharmaceutical composition further comprising least one pharmaceutically acceptable solvent, diluent and/or excipient.

4. The method according to claim 1, wherein the compound is effective in the prophylactic or therapeutic treatment of sepsis.

* * * * *

UNITED STATES PATENT AND TRADEMARK OFFICE
CERTIFICATE OF CORRECTION

PATENT NO. : 9,745,369 B2  
APPLICATION NO. : 14/405717  
DATED : August 29, 2017  
INVENTOR(S) : Antje Ostareck-Lederer et al.

Page 1 of 1

It is certified that error appears in the above-identified patent and that said Letters Patent is hereby corrected as shown below:

On the Title Page

Please add the following to the Assignee name and change the Country Code from Denmark to Germany:

(73) Assignee: Rheinisch-Westfalische Technische --Hochschule (RWTH) Aachen-- Aachen --(DE)--

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 2

<210> SEQ ID NO 1
<211> LENGTH: 79
<212> TYPE: PRT
<213> ORGANISM: Artificial Sequence
<220> FEATURE:
<223> OTHER INFORMATION: modulatory peptide

<400> SEQUENCE: 1

Gly Pro Ile Ile Thr Thr Gln Val Thr Ile Pro Lys Asp Leu Ala Gly
1               5                   10                  15

Ser Ile Ile Gly Lys Gly Gly Gln Arg Ile Lys Gln Ile Arg His Glu
            20                  25                  30

Ser Gly Ala Ser Ile Lys Ile Asp Glu Pro Leu Glu Gly Ser Glu Asp
        35                  40                  45

Arg Ile Ile Thr Ile Thr Gly Thr Gln Asp Gln Ile Gln Asn Ala Gln
    50                  55                  60

Tyr Leu Leu Gln Asn Ser Val Lys Gln Tyr Ser Gly Lys Phe Phe
65                  70                  75

<210> SEQ ID NO 2
<211> LENGTH: 38
<212> TYPE: RNA
<213> ORGANISM: Artificial Sequence
<220> FEATURE:
<223> OTHER INFORMATION: modulatory RNA
```

```
<400> SEQUENCE: 2
ccccacccuc uucccaagc cccacccucu uccccaag                    38
```